United States Patent
Dalrymple et al.

(10) Patent No.: US 6,525,241 B1
(45) Date of Patent: Feb. 25, 2003

(54) EXPRESSION METHODS

(75) Inventors: Michael Dalrymple, Dalgety Bay (GB); Lennart Lundberg, Billdal (SE); Mats Strömqvist, Umeå (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/355,295

(22) PCT Filed: Apr. 21, 1999

(86) PCT No.: PCT/SE99/00648

§ 371 (c)(1),
(2), (4) Date: Jul. 28, 1999

(87) PCT Pub. No.: WO99/54443

PCT Pub. Date: Oct. 28, 1999

(30) Foreign Application Priority Data

Apr. 22, 1998 (CH) .............................. 9801424

(51) Int. Cl.⁷ ...................... C12P 21/00; A01K 67/027; C12N 15/00
(52) U.S. Cl. ................ 800/7; 800/4; 800/16; 800/25
(58) Field of Search ............... 800/16, 4, 21, 800/7, 25; 435/69.1

(56) References Cited

U.S. PATENT DOCUMENTS 5,616,483 A    4/1997  Bjursell et al. ............. 435/198
5,716,817 A *  2/1998  Tornell ..................... 435/172.3

FOREIGN PATENT DOCUMENTS

WO    9420610    9/1994

OTHER PUBLICATIONS

Database:EST, Locus Accession No. A1274789, Nov. 1998.*
L Hansson et al., Journal of Biological Chemistry, "Recombinant Human Milk Bile Salt–stimulated Lipase," Dec. 1993, vol. 268, No. 35, pp. 26692–26698.*
C.–S. Wang et al., Biochemistry, "Isolation and Characterization of Human Milk Bile Salt–Activated Lipase C–Tail Fragment," 1995, 34:10639–19644.*
M Stromqvist et al., Transgenic Research, "Recombinant human bile salt–stimulated lipase: an example of defective O–glycosylation of a protein produced in milk of transgenic mice," 1996, 5: 475–485.*
Archives of Biochemistry and Biophysics, vol. 344, No. 1, Aug. 1997, Eva Landberg et al., "Glycosylation of Bile–Salt–Stimulated Lipase from Human Milk: Comparison of Native and Recombinant Forms" p. 94–p. 102.

* cited by examiner

Primary Examiner—Ram R. Shukla
(74) Attorney, Agent, or Firm—White & Case LLP

(57) ABSTRACT

The present invention relates to human bile salt-stimulated lipase (BSSL) obtainable from transgenic sheep. The invention further relates to transgenic sheep whose germ cells and somatic cells contain a recombinant nucleotide molecule comprising a nucleotide sequence encoding for human BSSL. The invention also relates to methods for producing said transgenic animals, as well as to methods for producing human BSSL derived from transgenic animals. In addition, the invention provides the use of compositions comprising BSSL in the treatment of diseases relating to exocrine pancreatic insufficiency, and for improvement of the utilization of dietary lipids in preterm born infants.

11 Claims, 4 Drawing Sheets

SEQUENCE LISTING

```
<160> NUMBER OF SEQ ID NOS: 5

<210> SEQ ID NO 1
<211> LENGTH: 11531
<212> TYPE: DNA
<213> ORGANISM: Homo sapiens
<220> FEATURE:
```

```
<223> OTHER INFORMATION: Genomic DNA
<220> FEATURE:
<223> OTHER INFORMATION: Mammary gland source
<220> FEATURE:
<221> NAME/KEY: CDS
<223> OTHER INFORMATION: join(1653..1727, 4071..4221, 4307..4429, 4707
      ..4904, 6193..6323, 6501..6608, 6751..6868, 8335
      ..8521, 8719..8922, 10124..10321, 10650..11394)
<221> NAME/KEY: mat_peptide
<223> OTHER INFORMATION: join(1722..1727, 4071..4221, 4307..4429, 4707
      ..4904, 6193..6323, 6501..6608, 6751..6868, 8335
      ..8521, 8719..8922, 10124..10321, 10650..11391)
<220> FEATURE:
<223> OTHER INFORMATION: /EC_number= 3.1.1.1
      /product= "Bile Salt-Stimulated Lipase"
<220> FEATURE:
<221> NAME/KEY: 5'UTR
<222> LOCATION: 1..1640
<220> FEATURE:
<221> NAME/KEY: TATA_signal
<222> LOCATION: 1611..1617
<220> FEATURE:
<221> NAME/KEY: exon
<222> LOCATION: 1641..1727
<220> FEATURE:
<221> NAME/KEY: exon
<222> LOCATION: 4071..4221
<220> FEATURE:
<221> NAME/KEY: exon
<222> LOCATION: 4307..4429
<220> FEATURE:
<221> NAME/KEY: exon
<222> LOCATION: 4707..4904
<220> FEATURE:
<221> NAME/KEY: exon
<222> LOCATION: 6193..6323
<220> FEATURE:
<221> NAME/KEY: exon
<222> LOCATION: 6501..6608
<220> FEATURE:
<221> NAME/KEY: exon
<222> LOCATION: 6751..6868
<220> FEATURE:
<221> NAME/KEY: exon
<222> LOCATION: 8335..8521
<220> FEATURE:
<221> NAME/KEY: exon
<222> LOCATION: 8719..8922
<220> FEATURE:
<221> NAME/KEY: exon
<222> LOCATION: 10124..10321
<220> FEATURE:
<221> NAME/KEY: exon
<222> LOCATION: 10650..11490
<220> FEATURE:
<221> NAME/KEY: 3'UTR
<222> LOCATION: 11491..11531

<400> SEQUENCE: 1
ggatccctcg aacccaggag ttcaagactg cagtgagcta tgattgtgcc actgcactct      60
agcctgggtg acagagaccc tgtctcaaaa aaacaaacaa acaaaaaacc tctgtggact     120
ccgggtgata atgacatgtc aatgtggatt catcaggtgt taacagctgt accccctggt     180
gggggatgtt gataacgggg gagactggag tggggcgagg acatacggga aatctctgta     240
atcttcctct aattttgctg tgaacctaaa gctgctctaa aaatgtacat agatataaac     300
tggggccttc ctttccctct gccctgcccc agccctcccc cacctccttc ctctccctgc     360
tgcctcccct ctgccctccc ctttcctcct tagccactgt aaatgacact gcagcaaagg     420
tctgaggcaa atgcctttgc cctggggcgc cccagccacc tgcaggcccc ttatttcctg     480
tggccgagct cctcctccca ccctccagtc ctttcccag cctccctcgc ccactaggcc      540
tcctgaattg ctggcaccgg ctgtggtcga cagacagagg gacagacgtg gctctgcagg     600
```

-continued

```
tccactcggt ccctggcacc ggccgcaggg gtggcagaac gggagtgtgg ttggtgtggg      660
aagcacaggc cccagtgtct cctggggac tgttgggtgg aaggctctg gctgccctca        720 ccctgttccc atcactgcag agggctgtgc ggtggctgga gctgccactg agtgtctcgg      780
tgagggtgac ctcacactgg ctgagcttaa aggccccatc tgaagacttt gttcgtggtg      840
ttctttcact tctcagagcc tttcctggct ccaggattaa tacctgttca cagaaaatac      900
gagtcgcctc ctcctccaca acctcacacg accttctccc ttccctcccg ctggcctctt      960
tccctcccct tctgtcactc tgcctgggca tgccccaggg cctcggctgg gccctttgtt     1020
tccacaggga aacctacatg gttgggctag atgcctccgc acccccccac ccacaccccc     1080
tgagcctcta gtcctccctc ccaggacaca tcaggctgga tggtgacact tccacacccct    1140 tgagtgggac tgccttgtgc tgctctggga ttcgcaccca gcttggacta cccgctccac     1200 gggcccagg  aaaagctcgt acagataagg tcagccacat gagtggaggg cctgcagcat     1260
gctgcccttt ctgtcccaga agtcacgtgc tcggtcccct ctgaagcccc tttggggacc    1320 tagggacaa  gcaggcatg  gagacatgga gacaaagtat gccctttct ctgacagtga     1380 caccaagccc tgtgaacaaa ccagaaggca gggcactgtg caccctgccc ggccccacca    1440 tccccttac  cacccgccac cttgccacct gcctctgctc ccaggtaagt ggtaacctgc    1500
acaggtgcac tgtgggtttg gggaaaactg gatctccctg cacctgaggg ggtagagggg    1560
agggagtgcc tgagagctca tgaacaagca tgtgaccttg gatccagctc cataaatacc    1620
cgaggcccag ggggagggcc acccagaggc tg atg ctc acc atg ggg cgc ctg     1673
                                    Met Leu Thr Met Gly Arg Leu
                                    -23             -20 caa ctg gtt gtg ttg ggc ctc acc tgc tgc tgg gca gtg gcg agt gcc      1721
Gln Leu Val Val Leu Gly Leu Thr Cys Cys Trp Ala Val Ala Ser Ala
    -15             -10                 -5 gcg aag gtaagagccc agcagagggg caggtcctgc tgctctctcg ctcaatcaga        1777
Ala Lys
  1 tctggaaact tcgggccagg ctgagaaaga gcccagcaca gccccgcagc agatcccggg     1837 cactcacgct catttctatg gggacaggtg ccaggtagaa cacaggatgc ccaattccat     1897 ttgaatttca gataaactgc caagaactgc tgtgtaagta tgtcccatgc aatatttgaa     1957 acaaatttct atgggccggg cgcagtggct cacacctgca atcccaccag tttgggaggc    2017 cgaggtgggt ggatcacttg aggtcaggag ttggagacca gcctggccaa catggtgaaa    2077 ccccgtctct actaaaaata caaatattaa tcgggcgtgg tggtgggtgc ctgtaatccc    2137 agctactcgg gaggctgagg caggagaacc gcttgaagct gggaggtgga gattgcggtg    2197 agctgagatc acgctactgc actccagcct gggtgacagg gcgagactct gtctcaaaaa    2257 atagaaaaag aaaaaaatga acatactaa aaaacaattc actgtttacc tgaaattcaa    2317 atgtaactgg gcctcttgaa tttacatttg ctaatcctgg tgattccacc taccaacctc    2377 tctgttgttc ccattttaca gaaggggaaa cgggcccagg ggcagggagt gtggagagca    2437 ggcagacggg tggagagaag caggcaggca gtttgcccag catggcacag ctgctgcctc    2497 ctattcctgt gcaggaagct gaaagccggg ctactccaca cccgggtccg ggtccctcca    2557 gaaagagagc cggcaggcag gagctctctc gaggcatcca taaattctac cctctctgcc    2617 tgtgaaggag aagccacaga aaccccaagc cccacaggaa gccggtgtcg gtgcccggcc    2677 cagtccctgc ccccagcagg agtcacacag gggacccccag atcccaacca cgctgttctg    2737 ctgcctgcgg tgtctcaggc cctggggact cctgtctcca cctctgctgc ctgctctcca    2797
```

```
cactccctgg ccctgggacc gggaggtttg ggcagtggtc ttgggctcct gactcaaagg    2857
agaggtcacc ttcttcttgg gcgagctctt cttggggtgc tgagaggcct tcggcaggtc    2917
atcacgaccc ctccccattt ccccaccctg aggccctctg ccagtctca attgcacagg     2977 gatcacgcca ctggcacaag gagacacaga tgcctcgcag gggatgccca cgatgcctgc    3037
atgtgttgct tctggttcct ttcctccagt tccaaccgcc gcactctccc acaccagtgt    3097 gacaggggc ccatcaccct agacttcaga gggctgctgg gaccctggct gggcctgggg     3157
gtgtagggcc accctgccct tccccacctg gaacctggca caggtgacag ccagcaagca    3217
atgacctggt cccaccatgc accacgggaa gagggagctg ctgcccaaga tggacaggag    3277
gtggcactgg ggcagacagc tgcttctcaa cagggtgact tcaagcccaa aagctgccca    3337
gcctcagttc cgtcagggac agagggtgga tgagcaccaa cctccaggcc cctcgtgggg    3397
gtggacagct tggtgcacag aggccatttt catggcacag ggaagcgtgg cggggtgggg    3457
aggtgtggtc cctaggggt tctttaccag caggggctc aggaactgtg gggacttggg      3517
catgggccca tcgactttgt gcccagccag ctaggccctg tgcagggaga tgggaggagg    3577
gaaaagcagg ccccacccct cagaaaggag gaaggttggt gtgaaacatc ccgggtacac    3637
tgagcattgg gtacactcct cccgggagct ggacaggcct cccatgtgat ggcaaacagg    3697
ccgacaggag acacggctgt tgctcgtctt ccacatggga aaactgagga tcggagtcaa    3757
agctgggcgg ccatagccag aacccaaacc tccatcccac ctcttggccg gcttccctag    3817
tgggaacact ggttgaacca gtttcctcta agattctggg agcaggacac ccccagggat    3877
aaggagagga acaggaatcc taaagccctg agcattgcag ggcaggggt gctgcctggg     3937 tctcctgtgc agagctgtcc tgctttgaag ctgtctttgc ctctgggcac gcggagtcgg    3997
cttgccttgc cccctccgga ttcaggccga tggggcttga gccccctga ccctgcccgt     4057 gtctccctcg cag ctg ggc gcc gtg tac aca gaa ggt ggg ttc gtg gaa        4106
              Leu Gly Ala Val Tyr Thr Glu Gly Gly Phe Val Glu
                 5                  10 ggc gtc aat aag aag ctc ggc ctc ctg ggt gac tct gtg gac atc ttc       4154
Gly Val Asn Lys Lys Leu Gly Leu Leu Gly Asp Ser Val Asp Ile Phe
 15                  20                  25                  30 aag ggc atc ccc ttc gca gct ccc acc aag gcc ctg gaa aat cct cag       4202
Lys Gly Ile Pro Phe Ala Ala Pro Thr Lys Ala Leu Glu Asn Pro Gln
             35                  40                  45 cca cat cct ggc tgg caa  g gtgggagtgg gtggtgccgg actggccctg           4251
Pro His Pro Gly Trp Gln
             50 cggcggggcg ggtgagggcg gctgccttcc tcatgccaac tcctgccacc tgcag  gg      4308
                                                              Gly acc ctg aag gcc aag aac ttc aag aag aga tgc ctg cag gcc acc atc       4356
Thr Leu Lys Ala Lys Asn Phe Lys Lys Arg Cys Leu Gln Ala Thr Ile
     55                  60                  65 acc cag gac agc acc tac ggg gat gaa gac tgc ctg tac ctc aac att       4404
Thr Gln Asp Ser Thr Tyr Gly Asp Glu Asp Cys Leu Tyr Leu Asn Ile
 70                  75                  80                  85 tgg gtg ccc cag ggc agg aag caa  g gtctgcctcc cctctactcc              4449
Trp Val Pro Gln Gly Arg Lys Gln
                 90 ccaagggacc ctcccatgca gccactgccc cgggtctact cctggcttga gtctggggc      4509 tgcaaagcta aacttccatg aaatcccaca gaggcgggga gggagcgcc cactgccgtt      4569 gcccagcctg ggcagggca gcgccttgga gcacctccct gtcttggccc caggcacctg     4629
```

-continued

```
ctgcacaggg acaggggacc ggctggagac agggccaggc ggggcgtctg gggtcaccag      4689
ccgctccccc atctcag tc tcc cgg gac ctg ccc gtt atg atc tgg atc         4738
                      Val Ser Arg Asp Leu Pro Val Met Ile Trp Ile
                       95                 100 tat gga ggc gcc ttc ctc atg ggg tcc ggc cat ggg gcc aac ttc ctc       4786
Tyr Gly Gly Ala Phe Leu Met Gly Ser Gly His Gly Ala Asn Phe Leu
105                 110                 115                 120 aac aac tac ctg tat gac ggc gag gag atc gcc aca cgc gga aac gtc       4834
Asn Asn Tyr Leu Tyr Asp Gly Glu Glu Ile Ala Thr Arg Gly Asn Val
                125                 130                 135 atc gtg gtc acc ttc aac tac cgt gtc ggc ccc ctt ggg ttc ctc agc       4882
Ile Val Val Thr Phe Asn Tyr Arg Val Gly Pro Leu Gly Phe Leu Ser
                140                 145                 150 act ggg gac gcc aat ctg cca  g gtgcgtgggt gccttcggcc ctgaggtggg       4934
Thr Gly Asp Ala Asn Leu Pro
              155 gcgaccagca tgctgagccc agcagggaga ttttcctcag cacccctcac cccaaacaac     4994 cagtggcggt tcacagaaag acccggaagc tggagtagaa tcatgagatg caggaggccc     5054 ttggtagctg tagtaaaata aaagatgctg cagaggccgg gagagatggc tcacgcctgt     5114 aatcccagca ctttaggagg cccacacagg tgggtcactt gagcgcagaa gttcaagacc     5174 agcctgaaaa tcactgggag accccatct ctacacaaaa attaaaaatt agctggggac      5234 tgggcgcggc ggctcacctc tgtaatccca gcacgttggg agcccaaggt gggtagatca     5294 cctgaggtca ggagtttgag accagcctga ctaaaatgga gaaacctctt ctctactaaa     5354 aatacaaaat tagccaggcg tggtggcgct tgcctgtaat cccagctact cgggaggctg     5414 aggcaggaga atcgcttgaa ctcaggaggc ggaggttgcg gtgagccgag atcatgccac     5474 tgcactccag cctggagaac aagagtaaaa ctctgtctca aaaaaaaaa aaaaaaaaa       5534 atagccaggc gtggtatctc atgcctctgt cctcagctac ctgggaggca gaggtggaag     5594 gatcgcttga gcccaggggt tcaaagctgc agtgagccgt ggtcgtgcca ctgcactcca     5654 gcctgggcga cagagtgagg ccccatctca aaaataagag gctgtgggac agacagacag     5714 gcagacaggc tgaggctcag agagaaacca ggagagcaga gctgagtgag agacagagaa     5774 caataccttg aggcagagac agctgtggac acagaagtgg caggacacag acaggaggga     5834 ctggggcagg ggcaggagag gtgcatgggc ctgaccatcc tgccccgac aaacaccacc      5894 ccctccagca ccacaccaac ccaacctcct ggggacccac cccatacagc accgcacccg     5954 actcagcctc ctgggaccca cccactccag caaccaacgt gacctagtct cctgggaccc     6014 accccctcca gcaccctacc cgacccagct tcttagggac ccaccatttg ccaactgggc     6074 tctgccatgg ccccaactct gttgagggca tttccacccc acctatgctg atctcccctc     6134 ctggaggcca ggcctgggcc actggtctct agcaccccct cccctgccct gccccag  gt    6194
                                                                  Gly
                                                                  160 aac tat ggc ctt cgg gat cag cac atg gcc att gct tgg gtg aag agg       6242
Asn Tyr Gly Leu Arg Asp Gln His Met Ala Ile Ala Trp Val Lys Arg
                165                 170                 175 aat atc gcg gcc ttc ggg ggg gac ccc aac aac atc acg ctc ttc ggg       6290
Asn Ile Ala Ala Phe Gly Gly Asp Pro Asn Asn Ile Thr Leu Phe Gly
                180                 185                 190 gag tct gct gga ggt gcc agc gtc tct ctg cag gtctcgggat ccctgtgggg     6343
Glu Ser Ala Gly Gly Ala Ser Val Ser Leu Gln
195                 200 agggcctgcc ccacaggttg agaggaagct caaacgggaa ggggagggtg gaggaggag      6403
```

-continued

| | |
|---|---|
| cgtggagctg gggctgtggt gctggggtgt ccttgtccca gcgtgggtg ggcagagtgg | 6463 |

```
ggagcggcct tggtgacggg atttctgggt cccgtag acc ctc tcc ccc tac aac     6518
                                        Thr Leu Ser Pro Tyr Asn
                                                        205 aag ggc ctc atc cgg cga gcc atc agc cag agc ggc gtg gcc ctg agt      6566
Lys Gly Leu Ile Arg Arg Ala Ile Ser Gln Ser Gly Val Ala Leu Ser
210             215                 220                 225 ccc tgg gtc atc cag aaa aac cca ctc ttc tgg gcc aaa aag              6608
Pro Trp Val Ile Gln Lys Asn Pro Leu Phe Trp Ala Lys Lys
                230                 235
```

| | |
|---|---|
| gtaaacggag gagggcaggg ctgggcgggg tgggggctgt ccacatttcc gttctttatc | 6668 |
| ctggacccca tccttgcctt caaatggttc tgagccctga gctccggcct cacctacctg | 6728 |

```
ctggccttgg ttctgccccc ag gtg gct gag aag gtg ggt tgc cct gtg ggt     6780
                           Val Ala Glu Lys Val Gly Cys Pro Val Gly
                                           240                 245 gat gcc gcc agg atg gcc cag tgt ctg aag gtt act gat ccc cga gcc      6828
Asp Ala Ala Arg Met Ala Gln Cys Leu Lys Val Thr Asp Pro Arg Ala
250             255                 260                 265 ctg acg ctg gcc tat aag gtg ccg ctg gca ggc ctg gag   t gtgagtagct   6878
Leu Thr Leu Ala Tyr Lys Val Pro Leu Ala Gly Leu Glu
                270                 275
```

| | |
|---|---|
| gctcgggttg gccatgggg tctcgagtg ggggttgagg gggtactgc cagggagtac | 6938 |
| tccggaggag agaggaaggt gccagagctg cggtcttgtc ctgtcaccaa ctagctggtg | 6998 |
| tctcccctcg aaggccccag ctgtaaggga gaggggggtgc cgtttcttct ttttttttga | 7058 |
| gatggagtct cactgttgcc caggctggag tgcagtgtca cgatctcagc tcactgcaac | 7118 |
| ctccacctcc tgggttcaag tgattctctg actcaacctc ccatgtagct gggactacag | 7178 |
| gcacatgcca ccatgcccag ataattttc tgtgtgttta gtagggatgg agtttcatcg | 7238 |
| tgttagctag gatgatctcg gtcttgggac ctcatgatct gcccacctcg gcctcccaaa | 7298 |
| gtgctggaat tacaggcgtg agccactgtg cccggcccct tctttattct tatctcccat | 7358 |
| gagttacaga ctcccctttg agaagctgat gaacatttgg ggcccctcc cccacctcat | 7418 |
| gcattcatat gcagtcattt gcatataatt ttagggagac tcatagacct cagaccaaga | 7478 |
| gcctttgtgc tagatgaccg ttcattcatt cgttcattca ttcagcaaac atttactgaa | 7538 |
| ccgtagcact ggggcccagc ctccagctcc actattctgt accccgggaa ggcctgggga | 7598 |
| cccattccac aaacacctct gcatgtcagc cttaccagct tgctacgcta aggctgtccc | 7658 |
| tcactcattc ttctatggca acatgccatg aagccaagtc atctgcacgt ttacctgaca | 7718 |
| tgagctcaac tgcacgggct ggacaagccc aaacaaagca accccacgg ccccgctaga | 7778 |
| agcaaaacct gctgtgctgg gcccagtgac agccaggccc cgcctgcctc agcagccact | 7838 |
| gggtcctcta gggccccgtc caggggtctg gagtacaatg cagacctccc accatttttg | 7898 |
| gctgatggac tggaacccag ccctgagaga gggagctcct tctccatcag ttccctcagt | 7958 |
| ggcttctaag tttcctcctt cctgcttcag gcccagcaaa gagagagagg agagggaggg | 8018 |
| gctgccgctg aagaggacag atctggccct agacagtgac tctcagcctg ggacgtgtg | 8078 |
| gcagggcctg gagacatctg tgattgtcac agctggggag gggtgctcc tggcacctcg | 8138 |
| tgggtcgagg ccggggatgc tctaaacatc tacagggca caggatgccc ctgatggtgc | 8198 |
| agaatcaacc ctgccccaag tgtccataga tcagagaagg gaggacatag ccaattccag | 8258 |
| ccctgagagg caaggggcgg ctcaggggaa actgggaggt acaagaacct gctaacctgc | 8318 |

```
tggctctccc acccag ac ccc atg ctg cac tat gtg ggc ttc gtc cct       8366
                  Tyr Pro Met Leu His Tyr Val Gly Phe Val Pro
                      280                 285 gtc att gat gga gac ttc atc ccc gct gac ccg atc aac ctg tac gcc    8414
Val Ile Asp Gly Asp Phe Ile Pro Ala Asp Pro Ile Asn Leu Tyr Ala
290                 295                 300                 305 aac gcc gcc gac atc gac tat ata gca ggc acc aac aac atg gac ggc    8462
Asn Ala Ala Asp Ile Asp Tyr Ile Ala Gly Thr Asn Asn Met Asp Gly
                310                 315                 320 cac atc ttc gcc agc atc gac atg cct gcc atc aac aag ggc aac aag    8510
His Ile Phe Ala Ser Ile Asp Met Pro Ala Ile Asn Lys Gly Asn Lys
            325                 330                 335 aaa gtc acg ga gtaagcaggg ggcacaggac tcagggcga cccgtgcggg          8561
Lys Val Thr Glu
            340 agggccgccg ggaaagcact ggcgaggggg ccagcctgga ggaggaaggc attgagtgga  8621 ggactgggag tgaggaagtt agcaccggtc ggggtgagta tgcacacacc ttcctgttgg  8681 cacaggctga gtgtcagtgc ctacttgatt cccccag g gag gac ttc tac aag     8734
                                           Glu Asp Phe Tyr Lys
                                                           345 ctg gtc agt gag ttc aca atc acc aag ggg ctc aga ggc gcc aag acg    8782
Leu Val Ser Glu Phe Thr Ile Thr Lys Gly Leu Arg Gly Ala Lys Thr
                350                 355                 360 acc ttt gat gtc tac acc gag tcc tgg gcc cag gac cca tcc cag gag    8830
Thr Phe Asp Val Tyr Thr Glu Ser Trp Ala Gln Asp Pro Ser Gln Glu
            365                 370                 375 aat aag aag aag act gtg gtg gac ttt gag acc gat gtc ctc ttc ctg    8878
Asn Lys Lys Lys Thr Val Val Asp Phe Glu Thr Asp Val Leu Phe Leu
380                 385                 390 gtg ccc acc gag att gcc cta gcc cag cac aga gcc aat gcc aa        8922
Val Pro Thr Glu Ile Ala Leu Ala Gln His Arg Ala Asn Ala Lys
395                 400                 405 gtgaggatct gggcagcggg tggctcctgg gggccttcct gggtgctgc accttccagc   8982 cgaggcctcg ctgtgggtgg ctctcaggtg tctgggttgt ctgggaaagt ggtgcttgag  9042
tccccacctg tgcctgcctg atccactttg ctgaggcctg gcaagacttg agggcctctt  9102
tttacctccc agcctacagg gctttacaaa ccctatgatc ctctgccctg ctcagccctg  9162 cacccccatgg tccttcccac tggagagttc ttgagctacc ttccatcccc catgctgtgt 9222 gcactgagag aacactggac aatagtttct atccactgac tcttatgggc ctcaactttg  9282
cccataattt cagcccacca ccacattaaa aatcttcatg taataatagc caattataat  9342
aaaaaataag gccagacaca gtagctcatg cctgtaatcc cagcacattg ggaggtcaag  9402
gtgggaggat cacttgaggt caggagtctg agactagtct ggccaacatg gcaaacccc   9462 atctctacta aaaatacaaa aattatccag gcatggtggt gcatgcctat aatcctagct  9522
actcaggagg ctgaggtagc agaattgatt gacccaggga ggtggaggtt gcagtgagcc  9582
gagattacgc cactgcactc cagcaggggc aacagagtga gactgtgtct cgaataaata  9642
agtaaataaa taataaaaat aaaaaataag ttaggaatac gaaaaagata ggaagataaa  9702
agtataccta gaagtctagg atgaaagctt tgcagcaact aagcagtaca tttagctgtg  9762
agcctccttt cagtcaaggc aaaaaggaaa acagttgagg gcctataacct tgtccaatct 9822 aattgaagaa tgcacattca cttggagagc aaaatatttc ttgatactga attctagaag  9882
gaaggtgcct cacaatgttt tgtggaggtg aagtataaat tcagctgaaa ttgtggaacc  9942
```

```
catgaatcca tgaatttggt tctcagcttt cccttccctg ggtgtaagaa gcccatctc   10002 ttcatgtgaa ttccccagac acttccctgc ccactgcccg ggacctccct ccaagtccgg  10062
tctctgggct gatcggtccc cagtgagcac cctgcctact tgggtggtct ctcccctcca  10122
g g agt gcc aag acc tac gcc tac ctg ttt tcc cat ccc tct cgg atg    10169
    Ser Ala Lys Thr Tyr Ala Tyr Leu Phe Ser His Pro Ser Arg Met
        410             415                 420 ccc gtc tac ccc aaa tgg gtg ggg gcc gac cat gca gat gac att cag    10217
Pro Val Tyr Pro Lys Trp Val Gly Ala Asp His Ala Asp Asp Ile Gln
425             430                 435                 440 tac gtt ttc ggg aag ccc ttc gcc acc ccc acg ggc tac cgg ccc caa    10265
Tyr Val Phe Gly Lys Pro Phe Ala Thr Pro Thr Gly Tyr Arg Pro Gln
                445                 450                 455 gac agg aca gtc tct aag gcc atg atc gcc tac tgg acc aac ttt gcc    10313
Asp Arg Thr Val Ser Lys Ala Met Ile Ala Tyr Trp Thr Asn Phe Ala
            460                 465                 470 aaa aca gg  gtaagacgtg ggttgagtgc agggcggagg gccacagccg            10361
Lys Thr Gly
        475 agaagggcct cccaccacga ggccttgttc cctcatttgc cagtggaggg actttgggca  10421 agtcacttaa cctcccctg catcggaatc catgtgtgtt tgaggatgag agttactggc   10481 agagccccaa gccatgcac gtgcacagcc agtgcccagt atgcagtgag ggcatggtg    10541 cccagggcca gctcagaggg cggggatggc tcaggcgtgc aggtggagag cagggcttca  10601 gcccctggg agtccccagc ccctgcacag cctcttctca ctctgcag g gac ccc      10656
                                                    Asp Pro aac atg ggc gac tcg gct gtg ccc aca cac tgg gaa ccc tac act acg    10704
Asn Met Gly Asp Ser Ala Val Pro Thr His Trp Glu Pro Tyr Thr Thr
            480                 485                 490 gaa aac agc ggc tac ctg gag atc acc aag aag atg ggc agc agc tcc    10752
Glu Asn Ser Gly Tyr Leu Glu Ile Thr Lys Lys Met Gly Ser Ser Ser
        495                 500                 505 atg aag cgg agc ctg aga acc aac ttc ctg cgc tac tgg acc ctc acc    10800
Met Lys Arg Ser Leu Arg Thr Asn Phe Leu Arg Tyr Trp Thr Leu Thr
510             515                 520                 525 tat ctg gcg ctg ccc aca gtg acc gac cag gag gcc acc cct gtg ccc    10848
Tyr Leu Ala Leu Pro Thr Val Thr Asp Gln Glu Ala Thr Pro Val Pro
                530                 535                 540 ccc aca ggg gac tcc gag gcc act ccc gtg ccc ccc acg ggt gac tcc    10896
Pro Thr Gly Asp Ser Glu Ala Thr Pro Val Pro Pro Thr Gly Asp Ser
            545                 550                 555 gag acc gcc ccc gtg ccg ccc acg ggt gac tcc ggg gcc ccc ccc gtg    10944
Glu Thr Ala Pro Val Pro Pro Thr Gly Asp Ser Gly Ala Pro Pro Val
        560                 565                 570 ccg ccc acg ggt gac tcc ggg gcc ccc ccc gtg ccg ccc acg ggt gac    10992
Pro Pro Thr Gly Asp Ser Gly Ala Pro Pro Val Pro Pro Thr Gly Asp
575             580                 585 tcc ggg gcc ccc ccc gtg ccg ccc acg ggt gac tcc ggg gcc ccc ccc    11040
Ser Gly Ala Pro Pro Val Pro Pro Thr Gly Asp Ser Gly Ala Pro Pro
590                 595                 600                 605 gtg ccg ccc acg ggt gac tcc ggg gcc ccc ccc gtg ccg ccc acg ggt    11088
Val Pro Pro Thr Gly Asp Ser Gly Ala Pro Pro Val Pro Pro Thr Gly
                610                 615                 620 gac tcc ggg gcc ccc ccc gtg ccg ccc acg ggt gac tcc ggc gcc ccc    11136
Asp Ser Gly Ala Pro Pro Val Pro Pro Thr Gly Asp Ser Gly Ala Pro
            625                 630                 635 ccc gtg ccg ccc acg ggt gac gcc ggg ccc ccc ccc gtg ccg ccc acg    11184
Pro Val Pro Pro Thr Gly Asp Ala Gly Pro Pro Pro Val Pro Pro Thr
        640                 645                 650
```

```
ggt gac tcc ggc gcc ccc ccc gtg ccg ccc acg ggt gac tcc ggg gcc    11232
Gly Asp Ser Gly Ala Pro Pro Val Pro Pro Thr Gly Asp Ser Gly Ala
    655                 660                 665 ccc ccc gtg acc ccc acg ggt gac tcc gag acc gcc ccc gtg ccg ccc    11280
Pro Pro Val Thr Pro Thr Gly Asp Ser Glu Thr Ala Pro Val Pro Pro
670             675                 680                 685 acg ggt gac tcc ggg gcc ccc cct gtg ccc ccc acg ggt gac tct gag    11328
Thr Gly Asp Ser Gly Ala Pro Pro Val Pro Pro Thr Gly Asp Ser Glu
                690                 695                 700 gct gcc cct gtg ccc ccc aca gat gac tcc aag gaa gct cag atg cct    11376
Ala Ala Pro Val Pro Pro Thr Asp Asp Ser Lys Glu Ala Gln Met Pro
        705                 710                 715 gca gtc att agg ttt tagcgtccca tgagccttgg tatcaagagg ccacaagagt    11431
Ala Val Ile Arg Phe
        720 gggaccccag gggctcccct cccatcttga gctcttcctg aataaagcct catacccctg    11491 tcggtgtctt tctttgctcc caaggctaag ctgcaggatc                         11531

<210> SEQ ID NO 2
<211> LENGTH: 2428
<212> TYPE: DNA
<213> ORGANISM: Homo sapiens
<220> FEATURE:
<223> OTHER INFORMATION: cDNA
<220> FEATURE:
<223> OTHER INFORMATION: Mammary gland source
<220> FEATURE:
<221> NAME/KEY: CDS
<222> LOCATION: 82..2319
<223> OTHER INFORMATION: /product= "bile salt-stimulated
      lipase"
<220> FEATURE:
<221> NAME/KEY: exon
<222> LOCATION: 985..1173
<220> FEATURE:
<221> NAME/KEY: exon
<222> LOCATION: 1174..1377
<220> FEATURE:
<221> NAME/KEY: exon
<222> LOCATION: 1378..1575
<220> FEATURE:
<221> NAME/KEY: exon
<222> LOCATION: 1576..2415
<220> FEATURE:
<221> NAME/KEY: mat_peptide
<222> LOCATION: 151..2316
<220> FEATURE:
<221> NAME/KEY: polyA_signal
<222> LOCATION: 2397..2402
<220> FEATURE:
<221> NAME/KEY: repeat_region
<222> LOCATION: 1756..2283
<220> FEATURE:
<221> NAME/KEY: 5'UTR
<222> LOCATION: 1..81
<220> FEATURE:
<221> NAME/KEY: repeat_unit
<222> LOCATION: 1756..1788
<220> FEATURE:
<221> NAME/KEY: repeat_unit
<222> LOCATION: 1789..1821
<220> FEATURE:
<221> NAME/KEY: repeat_unit
<222> LOCATION: 1822..1854
<220> FEATURE:
<221> NAME/KEY: repeat_unit
<222> LOCATION: 1855..1887
<220> FEATURE:
<221> NAME/KEY: repeat_unit
<222> LOCATION: 1888..1920
```

```
-continued

<220> FEATURE:
<221> NAME/KEY: repeat_unit
<222> LOCATION: 1921..1953
<220> FEATURE:
<221> NAME/KEY: repeat_unit
<222> LOCATION: 1954..1986
<220> FEATURE:
<221> NAME/KEY: repeat_unit
<222> LOCATION: 1987..2019
<220> FEATURE:
<221> NAME/KEY: repeat_unit
<222> LOCATION: 2020..2052
<220> FEATURE:
<221> NAME/KEY: repeat_unit
<222> LOCATION: 2053..2085
<220> FEATURE:
<221> NAME/KEY: repeat_unit
<222> LOCATION: 2086..2118
<220> FEATURE:
<221> NAME/KEY: repeat_unit
<222> LOCATION: 2119..2151
<220> FEATURE:
<221> NAME/KEY: repeat_unit
<222> LOCATION: 2152..2184
<220> FEATURE:
<221> NAME/KEY: repeat_unit
<222> LOCATION: 2185..2217
<220> FEATURE:
<221> NAME/KEY: repeat_unit
<222> LOCATION: 2218..2250
<220> FEATURE:
<221> NAME/KEY: repeat_unit
<222> LOCATION: 2251..2283

<400> SEQUENCE: 2
accttctgta tcagttaagt gtcaagatgg aaggaacagc agtctcaaga taatgcaaag      60
agtttattca tccagaggct g atg ctc acc atg ggg cgc ctg caa ctg gtt      111
                        Met Leu Thr Met Gly Arg Leu Gln Leu Val
                        -23         -20             -15 gtg ttg ggc ctc acc tgc tgc tgg gca gtg gcg agt gcc gcg aag ctg      159
Val Leu Gly Leu Thr Cys Cys Trp Ala Val Ala Ser Ala Ala Lys Leu
         -10             -5               1 ggc gcc gtg tac aca gaa ggt ggg ttc gtg gaa ggc gtc aat aag aag      207
Gly Ala Val Tyr Thr Glu Gly Gly Phe Val Glu Gly Val Asn Lys Lys
         5               10              15 ctc ggc ctc ctg ggt gac tct gtg gac atc ttc aag ggc atc ccc ttc      255
Leu Gly Leu Leu Gly Asp Ser Val Asp Ile Phe Lys Gly Ile Pro Phe
 20              25              30              35 gca gct ccc acc aag gcc ctg gaa aat cct cag cca cat cct ggc tgg      303
Ala Ala Pro Thr Lys Ala Leu Glu Asn Pro Gln Pro His Pro Gly Trp
             40              45              50 caa ggg acc ctg aag gcc aag aac ttc aag aag aga tgc ctg cag gcc      351
Gln Gly Thr Leu Lys Ala Lys Asn Phe Lys Lys Arg Cys Leu Gln Ala
             55              60              65 acc atc acc cag gac agc acc tac ggg gat gaa gac tgc ctg tac ctc      399
Thr Ile Thr Gln Asp Ser Thr Tyr Gly Asp Glu Asp Cys Leu Tyr Leu
         70              75              80 aac att tgg gtg ccc cag ggc agg aag caa gtc tcc cgg gac ctg ccc      447
Asn Ile Trp Val Pro Gln Gly Arg Lys Gln Val Ser Arg Asp Leu Pro
 85              90              95 gtt atg atc tgg atc tat gga ggc gcc ttc ctc atg ggg tcc ggc cat      495
Val Met Ile Trp Ile Tyr Gly Gly Ala Phe Leu Met Gly Ser Gly His
100             105             110             115 ggg gcc aac ttc ctc aac aac tac ctg tat gac ggc gag gag atc gcc      543
Gly Ala Asn Phe Leu Asn Asn Tyr Leu Tyr Asp Gly Glu Glu Ile Ala
             120             125             130
```

```
aca cgc gga aac gtc atc gtg gtc acc ttc aac tac cgt gtc ggc ccc       591
Thr Arg Gly Asn Val Ile Val Val Thr Phe Asn Tyr Arg Val Gly Pro
            135                 140                 145 ctt ggg ttc ctc agc act ggg gac gcc aat ctg cca ggt aac tat ggc       639
Leu Gly Phe Leu Ser Thr Gly Asp Ala Asn Leu Pro Gly Asn Tyr Gly
        150                 155                 160 ctt cgg gat cag cac atg gcc att gct tgg gtg aag agg aat atc gcg       687
Leu Arg Asp Gln His Met Ala Ile Ala Trp Val Lys Arg Asn Ile Ala
    165                 170                 175 gcc ttc ggg ggg gac ccc aac aac atc acg ctc ttc ggg gag tct gct       735
Ala Phe Gly Gly Asp Pro Asn Asn Ile Thr Leu Phe Gly Glu Ser Ala
180                 185                 190                 195 gga ggt gcc agc gtc tct ctg cag acc ctc tcc ccc tac aac aag ggc       783
Gly Gly Ala Ser Val Ser Leu Gln Thr Leu Ser Pro Tyr Asn Lys Gly
                200                 205                 210 ctc atc cgg cga gcc atc agc cag agc ggc gtg gcc ctg agt ccc tgg       831
Leu Ile Arg Arg Ala Ile Ser Gln Ser Gly Val Ala Leu Ser Pro Trp
            215                 220                 225 gtc atc cag aaa aac cca ctc ttc tgg gcc aaa aag gtg gct gag aag       879
Val Ile Gln Lys Asn Pro Leu Phe Trp Ala Lys Lys Val Ala Glu Lys
        230                 235                 240 gtg ggt tgc cct gtg ggt gat gcc gcc agg atg gcc cag tgt ctg aag       927
Val Gly Cys Pro Val Gly Asp Ala Ala Arg Met Ala Gln Cys Leu Lys
    245                 250                 255 gtt act gat ccc cga gcc ctg acg ctg gcc tat aag gtg ccg ctg gca       975
Val Thr Asp Pro Arg Ala Leu Thr Leu Ala Tyr Lys Val Pro Leu Ala
260                 265                 270                 275 ggc ctg gag tac ccc atg ctg cac tat gtg ggc ttc gtc cct gtc att      1023
Gly Leu Glu Tyr Pro Met Leu His Tyr Val Gly Phe Val Pro Val Ile
                280                 285                 290 gat gga gac ttc atc ccc gct gac ccg atc aac ctg tac gcc aac gcc      1071
Asp Gly Asp Phe Ile Pro Ala Asp Pro Ile Asn Leu Tyr Ala Asn Ala
            295                 300                 305 gcc gac atc gac tat ata gca ggc acc aac aac atg gac ggc cac atc      1119
Ala Asp Ile Asp Tyr Ile Ala Gly Thr Asn Asn Met Asp Gly His Ile
        310                 315                 320 ttc gcc agc atc gac atg cct gcc atc aac aag ggc aac aag aaa gtc      1167
Phe Ala Ser Ile Asp Met Pro Ala Ile Asn Lys Gly Asn Lys Lys Val
    325                 330                 335 acg gag gag gac ttc tac aag ctg gtc agt gag ttc aca atc acc aag      1215
Thr Glu Glu Asp Phe Tyr Lys Leu Val Ser Glu Phe Thr Ile Thr Lys
340                 345                 350                 355 ggg ctc aga ggc gcc aag acg acc ttt gat gtc tac acc gag tcc tgg      1263
Gly Leu Arg Gly Ala Lys Thr Thr Phe Asp Val Tyr Thr Glu Ser Trp
                360                 365                 370 gcc cag gac cca tcc cag gag aat aag aag aag act gtg gtg gac ttt      1311
Ala Gln Asp Pro Ser Gln Glu Asn Lys Lys Lys Thr Val Val Asp Phe
            375                 380                 385 gag acc gat gtc ctc ttc ctg gtg ccc acc gag att gcc cta gcc cag      1359
Glu Thr Asp Val Leu Phe Leu Val Pro Thr Glu Ile Ala Leu Ala Gln
        390                 395                 400 cac aga gcc aat gcc aag agt gcc aag acc tac gcc tac ctg ttt tcc      1407
His Arg Ala Asn Ala Lys Ser Ala Lys Thr Tyr Ala Tyr Leu Phe Ser
    405                 410                 415 cat ccc tct cgg atg ccc gtc tac ccc aaa tgg gtg ggg gcc gac cat      1455
His Pro Ser Arg Met Pro Val Tyr Pro Lys Trp Val Gly Ala Asp His
420                 425                 430                 435 gca gat gac att cag tac gtt ttc ggg aag ccc ttc gcc acc ccc acg      1503
Ala Asp Asp Ile Gln Tyr Val Phe Gly Lys Pro Phe Ala Thr Pro Thr
                440                 445                 450
```

```
ggc tac cgg ccc caa gac agg aca gtc tct aag gcc atg atc gcc tac    1551
Gly Tyr Arg Pro Gln Asp Arg Thr Val Ser Lys Ala Met Ile Ala Tyr
            455                 460                 465 tgg acc aac ttt gcc aaa aca ggg gac ccc aac atg ggc gac tcg gct    1599
Trp Thr Asn Phe Ala Lys Thr Gly Asp Pro Asn Met Gly Asp Ser Ala
        470                 475                 480 gtg ccc aca cac tgg gaa ccc tac act acg gaa aac agc ggc tac ctg    1647
Val Pro Thr His Trp Glu Pro Tyr Thr Thr Glu Asn Ser Gly Tyr Leu
    485                 490                 495 gag atc acc aag aag atg ggc agc agc tcc atg aag cgg agc ctg aga    1695
Glu Ile Thr Lys Lys Met Gly Ser Ser Ser Met Lys Arg Ser Leu Arg
500                 505                 510                 515 acc aac ttc ctg cgc tac tgg acc ctc acc tat ctg gcg ctg ccc aca    1743
Thr Asn Phe Leu Arg Tyr Trp Thr Leu Thr Tyr Leu Ala Leu Pro Thr
                520                 525                 530 gtg acc gac cag gag gcc acc cct gtg ccc ccc aca ggg gac tcc gag    1791
Val Thr Asp Gln Glu Ala Thr Pro Val Pro Pro Thr Gly Asp Ser Glu
            535                 540                 545 gcc act ccc gtg ccc ccc acg ggt gac tcc gag acc gcc ccc gtg ccg    1839
Ala Thr Pro Val Pro Pro Thr Gly Asp Ser Glu Thr Ala Pro Val Pro
        550                 555                 560 ccc acg ggt gac tcc ggg gcc ccc ccc gtg ccg ccc acg ggt gac tcc    1887
Pro Thr Gly Asp Ser Gly Ala Pro Pro Val Pro Pro Thr Gly Asp Ser
    565                 570                 575 ggg gcc ccc ccc gtg ccg ccc acg ggt gac tcc ggg gcc ccc ccc gtg    1935
Gly Ala Pro Pro Val Pro Pro Thr Gly Asp Ser Gly Ala Pro Pro Val
580                 585                 590                 595 ccg ccc acg ggt gac tcc ggg gcc ccc ccc gtg ccg ccc acg ggt gac    1983
Pro Pro Thr Gly Asp Ser Gly Ala Pro Pro Val Pro Pro Thr Gly Asp
                600                 605                 610 tcc ggg gcc ccc ccc gtg ccg ccc acg ggt gac tcc ggg gcc ccc ccc    2031
Ser Gly Ala Pro Pro Val Pro Pro Thr Gly Asp Ser Gly Ala Pro Pro
            615                 620                 625 gtg ccg ccc acg ggt gac tcc ggc gcc ccc ccc gtg ccg ccc acg ggt    2079
Val Pro Pro Thr Gly Asp Ser Gly Ala Pro Pro Val Pro Pro Thr Gly
        630                 635                 640 gac gcc ggg ccc ccc ccc gtg ccg ccc acg ggt gac tcc ggc gcc ccc    2127
Asp Ala Gly Pro Pro Pro Val Pro Pro Thr Gly Asp Ser Gly Ala Pro
    645                 650                 655 ccc gtg ccg ccc acg ggt gac tcc ggg gcc ccc ccc gtg acc ccc acg    2175
Pro Val Pro Pro Thr Gly Asp Ser Gly Ala Pro Pro Val Thr Pro Thr
660                 665                 670                 675 ggt gac tcc gag acc gcc ccc gtg ccg ccc acg ggt gac tcc ggg gcc    2223
Gly Asp Ser Glu Thr Ala Pro Val Pro Pro Thr Gly Asp Ser Gly Ala
                680                 685                 690 ccc cct gtg ccc ccc acg ggt gac tct gag gct gcc cct gtg ccc ccc    2271
Pro Pro Val Pro Pro Thr Gly Asp Ser Glu Ala Ala Pro Val Pro Pro
            695                 700                 705 aca gat gac tcc aag gaa gct cag atg cct gca gtc att agg ttt tagcgtccca    2326
Thr Asp Asp Ser Lys Glu Ala Gln Met Pro Ala Val Ile Arg Phe
        710                 715                 720 tagcgtccca tgagccttgg tatcaagagg ccacaagagt gggacccag gggctcccct cccatcttga    2386
gctcttcctg aataaagcct cataccccta aaaaaaaaa aa                       2428

<210> SEQ ID NO 3
<211> LENGTH: 745
<212> TYPE: PRT
<213> ORGANISM: Homo sapiens
```

```
<400> SEQUENCE: 3

Met Leu Thr Met Gly Arg Leu Gln Leu Val Leu Gly Leu Thr Cys
-23          -20              -15              -10

Cys Trp Ala Val Ala Ser Ala Ala Lys Leu Gly Ala Val Tyr Thr Glu
         -5              1               5

Gly Gly Phe Val Glu Gly Val Asn Lys Leu Gly Leu Leu Gly Asp
 10              15              20              25

Ser Val Asp Ile Phe Lys Gly Ile Pro Phe Ala Ala Pro Thr Lys Ala
             30              35              40

Leu Glu Asn Pro Gln Pro His Pro Gly Trp Gln Gly Thr Leu Lys Ala
             45              50              55

Lys Asn Phe Lys Lys Arg Cys Leu Gln Ala Thr Ile Thr Gln Asp Ser
             60              65              70

Thr Tyr Gly Asp Glu Asp Cys Leu Tyr Leu Asn Ile Trp Val Pro Gln
     75              80              85

Gly Arg Lys Gln Val Ser Arg Asp Leu Pro Val Met Ile Trp Ile Tyr
 90              95             100             105

Gly Gly Ala Phe Leu Met Gly Ser Gly His Gly Ala Asn Phe Leu Asn
                110             115             120

Asn Tyr Leu Tyr Asp Gly Glu Glu Ile Ala Thr Arg Gly Asn Val Ile
             125             130             135

Val Val Thr Phe Asn Tyr Arg Val Gly Pro Leu Gly Phe Leu Ser Thr
     140             145             150

Gly Asp Ala Asn Leu Pro Gly Asn Tyr Gly Leu Arg Asp Gln His Met
     155             160             165

Ala Ile Ala Trp Val Lys Arg Asn Ile Ala Ala Phe Gly Gly Asp Pro
170             175             180             185

Asn Asn Ile Thr Leu Phe Gly Glu Ser Ala Gly Gly Ala Ser Val Ser
             190             195             200

Leu Gln Thr Leu Ser Pro Tyr Asn Lys Gly Leu Ile Arg Arg Ala Ile
             205             210             215

Ser Gln Ser Gly Val Ala Leu Ser Pro Trp Val Ile Gln Lys Asn Pro
             220             225             230

Leu Phe Trp Ala Lys Lys Val Ala Glu Lys Val Gly Cys Pro Val Gly
 235             240             245

Asp Ala Ala Arg Met Ala Gln Cys Leu Lys Val Thr Asp Pro Arg Ala
250             255             260             265

Leu Thr Leu Ala Tyr Lys Val Pro Leu Ala Gly Leu Glu Tyr Pro Met
             270             275             280

Leu His Tyr Val Gly Phe Val Pro Val Ile Asp Gly Asp Phe Ile Pro
             285             290             295

Ala Asp Pro Ile Asn Leu Tyr Ala Asn Ala Ala Asp Ile Asp Tyr Ile
             300             305             310

Ala Gly Thr Asn Asn Met Asp Gly His Ile Phe Ala Ser Ile Asp Met
 315             320             325

Pro Ala Ile Asn Lys Gly Asn Lys Lys Val Thr Glu Glu Asp Phe Tyr
330             335             340             345

Lys Leu Val Ser Glu Phe Thr Ile Thr Lys Gly Leu Arg Gly Ala Lys
             350             355             360

Thr Thr Phe Asp Val Tyr Thr Glu Ser Trp Ala Gln Asp Pro Ser Gln
             365             370             375

Glu Asn Lys Lys Lys Thr Val Val Asp Phe Glu Thr Asp Val Leu Phe
 380             385             390
```

```
Leu Val Pro Thr Glu Ile Ala Leu Ala Gln His Arg Ala Asn Ala Lys
    395                 400                 405

Ser Ala Lys Thr Tyr Ala Tyr Leu Phe Ser His Pro Ser Arg Met Pro
410                 415                 420                 425

Val Tyr Pro Lys Trp Val Gly Ala Asp His Ala Asp Ile Gln Tyr
                430                 435                 440

Val Phe Gly Lys Pro Phe Ala Thr Pro Thr Gly Tyr Arg Pro Gln Asp
            445                 450                 455

Arg Thr Val Ser Lys Ala Met Ile Ala Tyr Trp Thr Asn Phe Ala Lys
                460                 465                 470

Thr Gly Asp Pro Asn Met Gly Asp Ser Ala Val Pro Thr His Trp Glu
        475                 480                 485

Pro Tyr Thr Thr Glu Asn Ser Gly Tyr Leu Glu Ile Thr Lys Lys Met
490                 495                 500                 505

Gly Ser Ser Ser Met Lys Arg Ser Leu Arg Thr Asn Phe Leu Arg Tyr
                510                 515                 520

Trp Thr Leu Thr Tyr Leu Ala Leu Pro Thr Val Thr Asp Gln Glu Ala
            525                 530                 535

Thr Pro Val Pro Pro Thr Gly Asp Ser Glu Ala Thr Pro Val Pro Pro
        540                 545                 550

Thr Gly Asp Ser Glu Thr Ala Pro Val Pro Pro Thr Gly Asp Ser Gly
    555                 560                 565

Ala Pro Pro Val Pro Pro Thr Gly Asp Ser Gly Ala Pro Pro Val Pro
570                 575                 580                 585

Pro Thr Gly Asp Ser Gly Ala Pro Pro Val Pro Pro Thr Gly Asp Ser
            590                 595                 600

Gly Ala Pro Pro Val Pro Pro Thr Gly Asp Ser Gly Ala Pro Pro Val
                605                 610                 615

Pro Pro Thr Gly Asp Ser Gly Ala Pro Pro Val Pro Pro Thr Gly Asp
            620                 625                 630

Ser Gly Ala Pro Pro Val Pro Pro Thr Gly Asp Ala Gly Pro Pro Pro
    635                 640                 645

Val Pro Pro Thr Gly Asp Ser Gly Ala Pro Pro Val Pro Pro Thr Gly
650                 655                 660                 665

Asp Ser Gly Ala Pro Pro Val Thr Pro Thr Gly Asp Ser Glu Thr Ala
                670                 675                 680

Pro Val Pro Pro Thr Gly Asp Ser Gly Ala Pro Pro Val Pro Pro Thr
            685                 690                 695

Gly Asp Ser Glu Ala Ala Pro Val Pro Pro Thr Asp Asp Ser Lys Glu
        700                 705                 710

Ala Gln Met Pro Ala Val Ile Arg Phe
    715                 720

<210> SEQ ID NO 4
<211> LENGTH: 722
<212> TYPE: PRT
<213> ORGANISM: Homo sapiens

<400> SEQUENCE: 4

Ala Lys Leu Gly Ala Val Tyr Thr Glu Gly Gly Phe Val Glu Gly Val
1               5                   10                  15

Asn Lys Lys Leu Gly Leu Leu Gly Asp Ser Val Asp Ile Phe Lys Gly
                20                  25                  30

Ile Pro Phe Ala Ala Pro Thr Lys Ala Leu Glu Asn Pro Gln Pro His
            35                  40                  45
```

-continued

```
Pro Gly Trp Gln Gly Thr Leu Lys Ala Lys Asn Phe Lys Lys Arg Cys
    50                  55                  60

Leu Gln Ala Thr Ile Thr Gln Asp Ser Thr Tyr Gly Asp Glu Asp Cys
65                  70                  75                  80

Leu Tyr Leu Asn Ile Trp Val Pro Gln Gly Arg Lys Gln Val Ser Arg
                85                  90                  95

Asp Leu Pro Val Met Ile Trp Ile Tyr Gly Gly Ala Phe Leu Met Gly
            100                 105                 110

Ser Gly His Gly Ala Asn Phe Leu Asn Asn Tyr Leu Tyr Asp Gly Glu
        115                 120                 125

Glu Ile Ala Thr Arg Gly Asn Val Ile Val Val Thr Phe Asn Tyr Arg
    130                 135                 140

Val Gly Pro Leu Gly Phe Leu Ser Thr Gly Asp Ala Asn Leu Pro Gly
145                 150                 155                 160

Asn Tyr Gly Leu Arg Asp Gln His Met Ala Ile Ala Trp Val Lys Arg
                165                 170                 175

Asn Ile Ala Ala Phe Gly Gly Asp Pro Asn Asn Ile Thr Leu Phe Gly
            180                 185                 190

Glu Ser Ala Gly Gly Ala Ser Val Ser Leu Gln Thr Leu Ser Pro Tyr
        195                 200                 205

Asn Lys Gly Leu Ile Arg Arg Ala Ile Ser Gln Ser Gly Val Ala Leu
    210                 215                 220

Ser Pro Trp Val Ile Gln Lys Asn Pro Leu Phe Trp Ala Lys Lys Val
225                 230                 235                 240

Ala Glu Lys Val Gly Cys Pro Val Gly Asp Ala Ala Arg Met Ala Gln
                245                 250                 255

Cys Leu Lys Val Thr Asp Pro Arg Ala Leu Thr Leu Ala Tyr Lys Val
            260                 265                 270

Pro Leu Ala Gly Leu Glu Tyr Pro Met Leu His Tyr Val Gly Phe Val
        275                 280                 285

Pro Val Ile Asp Gly Asp Phe Ile Pro Ala Asp Pro Ile Asn Leu Tyr
    290                 295                 300

Ala Asn Ala Ala Asp Ile Asp Tyr Ile Ala Gly Thr Asn Asn Met Asp
305                 310                 315                 320

Gly His Ile Phe Ala Ser Ile Asp Met Pro Ala Ile Asn Lys Gly Asn
                325                 330                 335

Lys Lys Val Thr Glu Glu Asp Phe Tyr Lys Leu Val Ser Glu Phe Thr
            340                 345                 350

Ile Thr Lys Gly Leu Arg Gly Ala Lys Thr Thr Phe Asp Val Tyr Thr
        355                 360                 365

Glu Ser Trp Ala Gln Asp Pro Ser Gln Glu Asn Lys Lys Thr Val
    370                 375                 380

Val Asp Phe Glu Thr Asp Val Leu Phe Leu Val Pro Thr Glu Ile Ala
385                 390                 395                 400

Leu Ala Gln His Arg Ala Asn Ala Lys Ser Ala Lys Thr Tyr Ala Tyr
                405                 410                 415

Leu Phe Ser His Pro Ser Arg Met Pro Val Tyr Pro Lys Trp Val Gly
            420                 425                 430

Ala Asp His Ala Asp Asp Ile Gln Tyr Val Phe Gly Lys Pro Phe Ala
        435                 440                 445

Thr Pro Thr Gly Tyr Arg Pro Gln Asp Arg Thr Val Ser Lys Ala Met
    450                 455                 460
```

-continued

```
Ile Ala Tyr Trp Thr Asn Phe Ala Lys Thr Gly Asp Pro Asn Met Gly
465                 470                 475                 480

Asp Ser Ala Val Pro Thr His Trp Glu Pro Tyr Thr Thr Glu Asn Ser
            485                 490                 495

Gly Tyr Leu Glu Ile Thr Lys Lys Met Gly Ser Ser Ser Met Lys Arg
            500                 505                 510

Ser Leu Arg Thr Asn Phe Leu Arg Tyr Trp Thr Leu Thr Tyr Leu Ala
        515                 520                 525

Leu Pro Thr Val Thr Asp Gln Glu Ala Thr Pro Val Pro Pro Thr Gly
        530                 535                 540

Asp Ser Glu Ala Thr Pro Val Pro Pro Thr Gly Asp Ser Glu Thr Ala
545                 550                 555                 560

Pro Val Pro Pro Thr Gly Asp Ser Gly Ala Pro Pro Val Pro Pro Thr
                565                 570                 575

Gly Asp Ser Gly Ala Pro Pro Val Pro Pro Thr Gly Asp Ser Gly Ala
            580                 585                 590

Pro Pro Val Pro Pro Thr Gly Asp Ser Gly Ala Pro Pro Val Pro Pro
        595                 600                 605

Thr Gly Asp Ser Gly Ala Pro Pro Val Pro Pro Thr Gly Asp Ser Gly
    610                 615                 620

Ala Pro Pro Val Pro Pro Thr Gly Asp Ser Gly Ala Pro Pro Val Pro
625                 630                 635                 640

Pro Thr Gly Asp Ala Gly Pro Pro Val Pro Pro Thr Gly Asp Ser
                645                 650                 655

Gly Ala Pro Pro Val Pro Pro Thr Gly Asp Ser Gly Ala Pro Pro Val
            660                 665                 670

Thr Pro Thr Gly Asp Ser Glu Thr Ala Pro Val Pro Pro Thr Gly Asp
        675                 680                 685

Ser Gly Ala Pro Pro Val Pro Pro Thr Gly Asp Ser Glu Ala Ala Pro
    690                 695                 700

Val Pro Pro Thr Asp Asp Ser Lys Glu Ala Gln Met Pro Ala Val Ile
705                 710                 715                 720

Arg Phe
    722

<210> SEQ ID NO 5
<211> LENGTH: 11
<212> TYPE: PRT
<213> ORGANISM: Homo sapiens

<400> SEQUENCE: 5

Pro Val Pro Pro Thr Gly Asp Ser Gly Ala Pro
1               5                   10
```

EXPRESSION METHODS

TECHNICAL FIELD

The present invention relates to human bile salt-stimulated lipase (BSSL) obtainable from transgenic sheep. The invention further relates to transgenic sheep whose germ cells and somatic cells contain a recombinant nucleotide molecule comprising a nucleotide sequence encoding for human BSSL. The invention also relates to methods for producing said transgenic animals, as well as to methods for producing human BSSL derived from transgenic animals. In addition, the invention provides the use of compositions comprising BSSL in the treatment of diseases relating to exocrine pancreatic insufficiency, and for improvement of the utilization of dietary lipids in preterm born infants.

BACKGROUND ART

Human Bile Salt-Stimulated Lipase

Bile Salt-Stimulated Lipase (BSSL) is the major lipolytic activity present in human milk (Wang & Johnson, 1983; Wang & Hartsuck, 1993). As its name implies, the enzyme is not active in the milk but is activated in the intestine by bile salts. In mammals a similar enzyme activity is also secreted from the pancreas into the intestine. The cDNA sequences for both the mammary and pancreatic enzyme are identical indicating that they are the product of a single gene (Reue et al., 1991; Lidberg et al., 1992). BSSL shares with other pancreatic lipases a triacylglycerol hydrolase activity but BSSL is the only intestinal lipase which hydrolyses cholesterol ester and other fatty acid esters, such as vitamin A ester. The protein is stable to both proteases and the acid environment in infant stomachs. These unique activities and the large quantity of BSSL in human milk suggest that this enzyme is physiologically important.

The cDNA sequence (SEQ ID NO: 2) and deduced amino acid sequence (SEQ ID NOS: 3and 4) of BSSL have been disclosed by Nilsson et al. (1990); in U.S. Pat. No. 5,200,183 (Oklahoma Medical Research Foundation); and in WO 91/18923 (Astra AB). Human BSSL is a glycoprotein consisting of 772 amino acids. The C-terminal portion is composed of 16 repeats each of 11 amino acids having consensus PVPPTGDSGAP (SEQ ID NO: 5). The genomic DNA sequence (SEQ ID NO: 1) encoding human BSSL is disclosed by Lidberg et al. (1992) in U.S. Pat. No. 5,616,483 (Astra AB).

BSSL is heavily glycosylated, with one potential N-linked glycosylation site (Asp187) and two potential O-linked sites per repeat (Baba et al., 1991). Even though the glycosylation state of the enzyme is not critical for activity in vitro (Hansson et aL, 1993), O-glycosylation nevertheless appears important for the biological function of BSSL. Loomes et al. (1997) have suggested that the C-terminal repeat region is important for prevention of non-specific hydrophobic interactions and that it counteracts a tendency of BSSL to self-aggregate. Wang et al. (1995) have shown that the repeat region contains different Lewis antigens, suggesting that it may also contribute to adhesive activity in the physiological function of BSSL. Spilburg et al. (1995) and Bosner et al. (1988) have suggested that the C-terminal domain may be important for heparin binding and interactions with proteoglycans on cell surfaces. Immunohistochemical experiments on mouse, rat and human tissues have indicated binding of the BSSL protein to intestinal cell membranes. O-glycosylation might thus be important for such binding of BSSL to a "BSSL-receptor" in the intestine and for proper physiological function of the enzyme.

The expression of both cDNA and genomic constructs for BSSL, from the murine whey acidic protein (WAP) promoter, in the milk of transgenic mice have been disclosed (Strömqvist et al., 1995). Levels of up to 1 mg/ml were obtained in milk and the protein was 100% active in vitro. However, the transgenic form of the enzyme exhibited a considerably reduced glycosylation state when compared to native enzyme or enzyme produced in cell culture. Recombinant human BSSL derived from transgenic mice apparently lacked the O-glycosylation pattern of native human enzyme.

Expression of Heterologous Proteins in the Milk of Transgenic Animals

The cloning and characterization of the ovine β-lactoglobulin (BLG) gene has been disclosed by Ali and Clark, 1988. It was demonstrated that BLG is consistently expressed at high levels in the milk of mice made transgenic for the entire gene (Simons et al., 1987; Harris et al., 1991). Further experiments demonstrated that the BLG promoter region can direct high levels of expression of a heterologous human protein to the milk of transgenic mice (Archibald et al., 1990). The generation of transgenic sheep, expressing human proteins in their milk using the BLG gene to drive expression, indicated that this technology might be viable as a commercial production route (Simons et al., 1988; Clark et al., 1989). The feasibility of applying this technology to the modification of livestock milks has been confirmed, demonstrating high level expression of human alpha-1-antitrypsin in the milk of transgenic sheep (Wright et al., 1991; Carver et al., 1992; Carver et al., 1993; Cooper and Dalrymple, 1994). This high level expression of a heterologous protein in livestock milk was the result of using a fusion of the BLG promoter region to human genomic sequences (Wright et al., 1991). The vector pMAD6, disclosed in U.S. Pat No. 5,639,940, has been designed to express genes from the BLG promoter.

DISCLOSURE OF THE INVENTION

Figure 1:
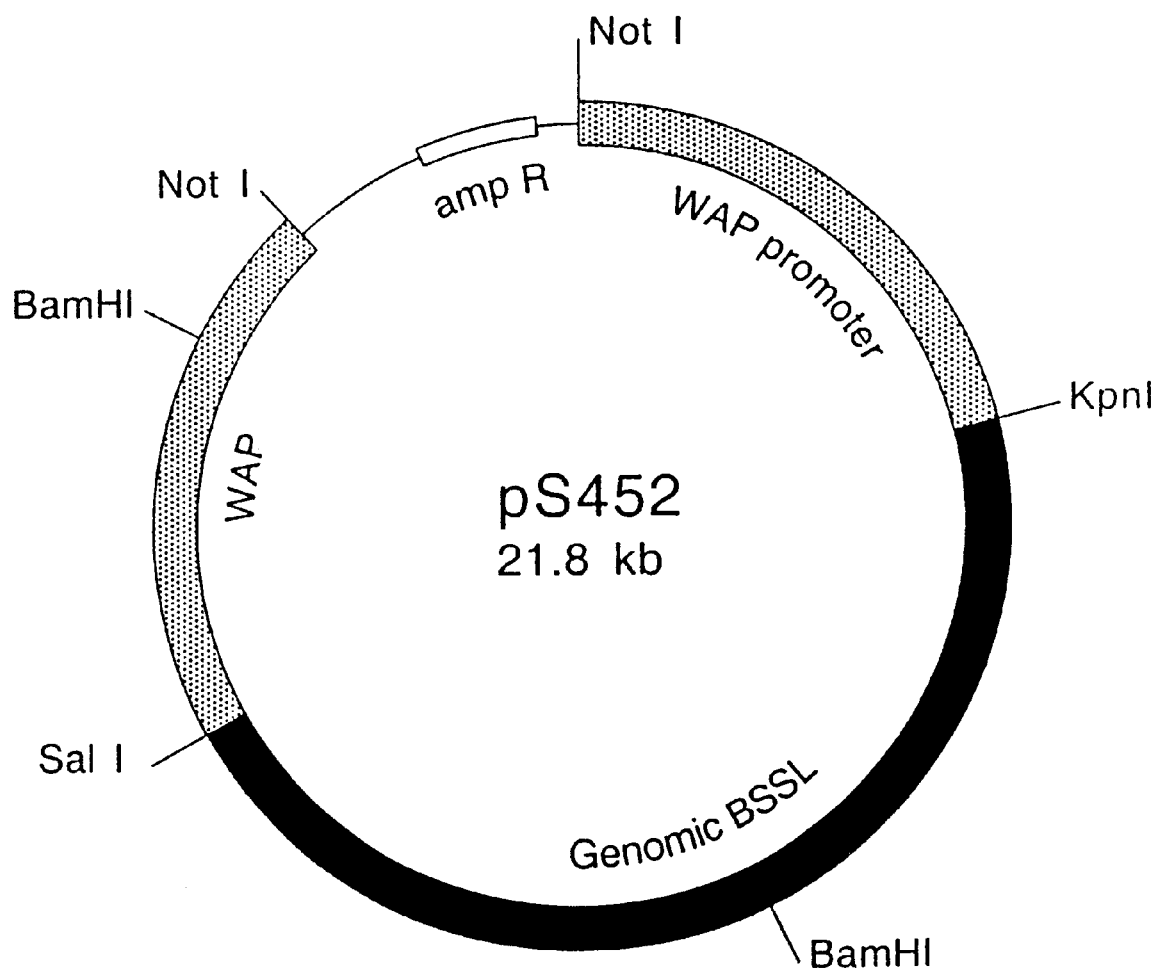
FIG. 1. Structure of plasmid pS452.

It has surprisingly been shown that human bile salt-stimulated lipase (BSSL), produced in the mammary gland of transgenic sheep, has a distinct O-glycosylation pattern, which is in contrast to previous forms of BSSL produced in transgenic animals, and which may be important for the biological function of BSSL.

The gene for human bile salt-stimulated lipase has been placed under the transcriptional control of the ovine β-lactoglobulin promoter and introduced into sheep. This resulted in the production of thirteen transgenic animals from 206 livebirths. Four transgenics were females. After inducing lactation in ewe lambs, expression of the transgene has been detected in the mammary gland and a range of levels of BSSL protein secreted into the milk. Expression levels in excess of 3 g/l have been detected, a level which could form the basis of commercial production of human BSSL. The protein is fully active, carries glycosylation, and show the same enzyme characteristics as the native protein and the mammalian cell culture produced variants.

Consequently, in a first aspect, the invention provides recombinant human bile salt-stimulated lipase (BSSL) produced by a transgenic non-human mammal, said lipase being glycosylated to at least 5%. The transgenic non-human mammal could be an ungulate placental mammal.

In another aspect of the invention, the recombinant human BSSL is having a total monosaccharide content of above 10%. In yet another aspect, the recombinant human BSSL comprises at least 1% N-acetylgalactosamine.

In one embodiment of the invention, the recombinant human BSSL is characterised in comprising substantially the following monosaccharide composition: 0–6% fucose; 3–12% galactose; 0.1–2% mannose; 1–7% N-acetylgalactosamine; 0.5–15% N-acetylglucosamine; and 1.5–10% 5-Ac-neuraminic acid.

In another aspect of this embodiment of the invention, the recombinant human BSSL is characterised in comprising substantially the following monosaccharide composition: 0–1% fucose; 6.5–8.5% galactose; 1–2% mannose; 5.5–7% N-acetylgalactosamine; 3.5–5% N-acetylglucosamine; and 2.5–4% 5-Ac-neuraminic acid. Preferably, the human BSSL comprises substantially the monosaccharide composition as shown in row 1 of Table IV. The recombinant bile salt-stimulated lipase according to the invention has substantially the amino acid sequence set forth as SEQ ID NO: 3 or SEQ ID NO: 4 in the Sequence Listing, or is comprising the amino acid sequence consisting functionally of SEQ ID NO: 3 or SEQ ID NO: 4 in the Sequence Listing.

In another aspect, the invention provides a transgenic sheep whose germ cells and somatic cells contain a recombinant nucleotide molecule introduced into the said sheep, or an ancestor of said sheep, at an embryonic stage, said recombinant nucleotide molecule comprising (i) a nucleotide sequence encoding for human BSSL and (ii) a promoter operatively linked to the said nucleotide sequence encoding for human BSSL.

In the tranogenic sheep according to the invention, the nucleotide sequence encoding for human BSSL can be introduced as a genomic sequence including introns (SEQ ID NO: 1) or as cDNA (SEQ ID NO: 2). It has been reported that sequences comprising introns are preferable for regulated gene expression in transgenic animals (Brinster et al., 1998; Whitelaw et al., 1991. The plasmid pS452 (deposited under accession number DSM 7449 at DSM-Deutsche Sammlung von Mikroorganismen und Zellkulturen GmbH, Mascheroder Weg 1B, D-3300 Braunschweig, Germany) has a genomic fragment of BSSL (SEQ ID NO: 1) inserted into the first exon of the murine WAP gene.

Consequently, the nucleotide sequence encoding for human BSSL may be of genomic or synthetic origin or any combination thereof. Specifically, the said nucleotide sequence can be selected from:

(a) a nucleotide sequence carried by the plasmid pS452, identified by accession number DSM 7499;

(b) a nucleotide sequence set forth as SEQ ID NO: 1 or SEQ ID NO: 2 in the Sequence Listing;

(c) a nucleotide sequence encoding a polypeptide set forth as SEQ ID NO: 3 or SEQ ID NO: 4 in the Sequence Listing;

(d) a nucleotide sequence which hybridizes with any of the sequences defined in (a), (b) or (c) under stringent hybridization conditions.

The term "stringent hybridization conditions" is known in the art from standard protocols (e.g. Ausubel et al., supra) and could be understood as e.g. hybridization to filter-bound DNA in 0.5 M $NaHPO_4$, 7% sodium dodecyl sulfate (SDS), 1 mM EDTA at +65° C., and washing in 0.×SSC/0.1% SDS at +68° C.

It will be understood by the skilled person that for expression of the BSSL gene in the mammary gland of the transgenic sheep according to the invention, the nucleotide sequence coding for human BSSL should be linked to a gene encoding a milk protein, or a it subsequence thereof, capable of mediating and targeting the expression of the BSSL gene to the mammary gland. In particular, there should be a promoter operatively linked to the said nucleotide sequence encoding for human bile salt-stimulated lipase. The said promoter can e.g. be the BSSL promoter, whey acidic protein promoter, or a milk protein promoter, such as a casein promoter, (α-lactalbumin promoter or, preferably, a β-lactoglobulin promoter.

The milk protein gene to be used may be derived from the same species as the one in which the expression system is to be inserted, or it may be derived from another species. It has been shown that the regulatory elements that target gene expression to the mammary gland are functional across species boundaries (Hennighausen et al., 1990).

The mammary gland as a tissue of expression, as well as the use of genes encoding milk proteins, are generally considered to be particularly suitable for use in the production of heterologous proteins in transgenic non-human mammals, since milk proteins are naturally produced at high expression levels in the mammary gland. In addition, milk is readily collected and available in large quantities. In the present invention, the use of milk protein genes in the production of human BSSL has the further advantage that BSSL is produced under conditions similar to the natural production conditions in terms of regulation of expression and production location (the mammary gland). The signal peptide necessary for the secretion of BSSL into milk is shown as −23 to −1 in SEQ ID NO: 3.

Consequently, a further aspect of the invention is a female transgenic sheep wherein the nucleotide sequence encoding for bile salt-stimulated lipase is expressed in the mammary gland of the said female transgenic sheep, and wherein bile salt-stimulated lipase is present in the milk of the said female transgenic sheep.

Included in the invention is a process for production of a female transgenic sheep comprising:

(a) providing a gene encoding for human bile salt-stimulated lipase operatively linked to a promoter functional in a sheep;

(b) introducing said gene into an embryo or fertilized egg of a sheep, so as to incorporate said gene into the germline of the said sheep:

(c) transplanting said embryo or fertilized egg into a pseudopregnant host sheep;

(d) allowing said host sheep to produce progeny;

(e) selecting a female progeny sheep that produces recoverable amounts of bile salt-stimulated lipase in its milk.

The promoter mentioned in step (a) can e.g. be the BSSL promoter, whey acidic protein promoter, or or a milk protein promoter, such as a casein promoter, α-lactalbumin promoter or, preferably, a β-lactoglobulin promoter.

Several methods can be used to introduce exogenous DNA into the developing mammalian embryo in such a way that it may ultimately become stably integrated into a chromosome of the resulting animal (e.g. Hogan et al., 1994; Umland et al., 1996).

(a) The gene may be directly injected into a fertilized egg, e.g. a fertilized single cell egg or a pro-nucleus thereof, or an embryo of the sheep, by physically injecting it through a microscopically small-bore glass needle. The microinjected eggs may then subsequently be transferred into the oviducts of pseudopregnant foster mothers and allowed to develop. Normally, not all of the injected eggs will develop into adult females expressing human BSSL. Thus, about half of the marmmals will from a statistically point of view be males from which, however, females can be bred in the following generations. Once integrated in the germ line, the gene encoding for human BSSL may be expressed at high levels to produce a correctly processed and functional human BSSL in stable lines of the mammal in question.

Direct microinjection is labor intensive and technically demanding but would appear to have few limitations on the type or size of DNA that can be introduced. Within the last three years there have been several papers which describe the introduction of hundreds of kilobase pairs of contiguous DNA, in the form of yeast artificial chromosomes, into the mouse germ line (Schedl et al., 1993; Fujiwara et al., 1997; Manson et al., 1997).

(b) Retroviruses can be genetically modified to act as vectors allowing the infection of embryos with exogenous DNA (Jaenisch et al., 1975; Gilboa et al., 1986).

(c) Sperm has been claimed as an efficient mediator of exogenous gene transfer into mammalian embryos by one group (Lavitrano et al., 1989).

(d) DNA recombination, homologous or non-specific, in embryonic stem cells can also be used to permanently modify the germline. Stem cells are pluripotent or totipotent cells derived from a mammalian embryo that are able to be grown in culture and which can contribute to a developing embryo (Evans & Kaufman, 1981; Robertson, 1987). The resulting animal possesses a number of cells derived from the embryonic stem cells, some of which may populate the germline and result in transmission of genetic material to the offspring (Robertson, 1987). Embryonic stem cells can also be genetically manipulated whilst in culture. DNA can be introduced into the cells using a variety of techniques (e.g. electroporation, lipofection, microinjection, retroviral infection and calcium phosphate precipitation). By employing the antibiotic G418, or exploiting the biochemistry of the enzyme thymidine kinase, transformed cells, that have incorporated exogenous DNA in a specific or non-specific way, can be positively and negatively selected (Bradley, 1991; Hooper, 1992). Very subtle alterations of the genome are possible, such as point mutations, as well as the generation of specific deletions (so-called "knock outs", e.g. Stacey et al., 1994) or replacements (Stacey et al., 1994; Stacey et al., 1995). However, to date this method has only been successful in the mouse. Embryonic stem cells have only demonstrably been isolated from murine embryos, the search in other species continues (McWhir et al., 1996).

(e) In vitro manipulation of somatic or other cells (e.g. using homologous recombination as above) followed by the generation of an animal by nuclear transfer. Wilmut and co-workers (Wilmut et al., 1997) described the successful cloning of a sheep by nuclear transfer from both foetal and adult cells. The adult cell in question was derived from a line which had been grown in vitro for many passages. This new technology takes an enucleated, unfertilized, egg and places another cell into the space between the zona pellucida and the cytoplasmic membrane. The membranes of the two cells are fused with an electric pulse. Reconstructed embryos are allowed a brief development period in a temporary sheep recipient before final evaluation and introduction into a synchronized ewe.

Thus, it is conceivable that adult or foetal livestock cells can be manipulated in vitro, with much the same technology as is used for the alteration of murine embryonic stem cells, and then used to generate transgenic animals. Indeed, there are now transgenic sheep which have been made by such an approach, whereby a human gene under the control of BLG has been introduced into cells in vitro, prior to nuclear transfer (Schnieke et al., 1997).

In a further aspect, the invention provides a process for production of human bile salt-stimulated lipase comprising:
　(a) producing milk in a female transgenic sheep as defined above;
　(b) collecting the milk produced in step (a); and, optionally,
　(c) isolating the bile salt-stimulated lipase.

More specifically, the said process for production of human bile salt-stimulated lipase can comprise:
　(a) providing a gene encoding for human bile salt-stimulated lipase operatively linked to a promoter functional in a sheep;
　(b) introducing said gene into an embryo or fertilized egg of a sheep, so as to incorporate said gene into the germline of the said sheep:
　(c) transplanting said embryo or fertilized egg into a pseudopregnant host sheep;
　(d) allowing said host sheep to produce progeny;
　(e) selecting a female progeny sheep that produces recoverable amounts of bile salt-stimulated lipase in its milk;
　(f) collecting the milk produced by the female sheep selected in step (e); and, optionally,
　(g) isolating the bile salt-stimulated lipase.

The promoter mentioned in step (a) can e.g. be the BSSL promoter, whey acidic protein promoter, or a milk protein promoter, such as a casein promoter, α-lactalbumin promoter or, preferably, a β-lactoglobulin promoter.

In the above mentioned processes for production of a female transgenic sheep, or for production of human BSSL, the said gene encoding for bile salt-stimulated lipase can preferably have a nucleotide sequence selected from
　(a) a nucleotide sequence carried by the plasmid pS452, identified by accession number DSM 7499;
　(a) nucleotide sequence set forth as SEQ ID NO: 1 or SEQ ID NO: 2 in the Sequence Listing;
　(c) a nucleotide sequence encoding for a polypeptide set forth as SEQ ID NO: 3 or SEQ ID NO: 4 in the Sequence Listing;
　(d) a nucleotide sequence which hybridizes with any of the sequences defined in (a), (b) or (c) under stringent hybridization conditions.

The invention includes recombinant human BSSL obtainable by the above mentioned processes for producing human BSSL, recombinant human bile salt-stimulated lipase (BSSL) produced by a transgenic non-human mammal, said lipase being glycosylated to at least 5%. The said recombinant human BSSL may have a total monosaccharide content of above 10%, and/or may comprise at least 1% N-acetylgalactosamine. The said recombinant human BSSL is characterised in comprising substantially the following monosaccharide composition: 0–6% fucose; 3–12% galactose; 0.1–2% mannose; 1–7% N-acetylgalactosamine; 0.5–15% N-acetylglucosamine; and 1.5–10% 5-Ac-neuraminic acid. In another aspect the recombinant human BSSL is characterised in comprising substantially the following monosaccharide composition: 0–1% fucose; 6.5–8.5% galactose; 1–2% mannose; 5.5–7% N-acetylgalactosamine; 3.5–5% N-acetylglucosamine; and 2.5–4% 5-Ac-neuraminic acid. More preferably, the said human BSSL comprises substantially the following monosaccharide composition: 0–1% fucose; 6.5–8.5% galactose; 1–2% mannose; 5.5–7% N-acetylgalactosamine; 3.5–5% N-acetylglucosamine; and 2.5–4% 5-Ac-neuraminic acid. Most preferably, the human BSSL comprises substantially the monosaccharide composition as shown in row 1 of Table IV. Preferably, the recombinant bile salt-stimulated lipase according to the invention has substantially the amino acid sequence set forth as SEQ ID NO: 3 or SEQ ID NO: 4 in the Sequence Listing.

In another aspect, the present invention provides a pharmaceutical preparation comprising human BSSL derived from the transgenic as described above. The preparation may be prepared by adding the recombinant human BSSL in a purified or partly purified form to the normal constituents of a pharmaceutical preparation, such as a pharmaceutically acceptable carrier.

In yet another aspect, the invention provides the use of the bile salt-stimulated lipase described above in the manufacture of a medicament for the treatment of a pathological condition related to exocrine pancreatic insufficiency, e.g. in cystic fibrosis. Included in the invention is also the use of bile salt-stimulated lipase as described above in the manufacture of a medicament for the improvement of the utilization of dietary lipids in preterm born infants.

The invention also provides a method for treatment of a pathological condition related to exocrine pancreatic insufficiency, e.g. in cystic fibrosis, which comprises administering to a mammal, including man, in need of such treatment an effective amount of bile salt-stimulated lipase as described above. The term "effective amount" should in this context be understood as that amount required to restore fat digestion and repair the physiological deficit. Included in the invention is also a method for the improvement of the utilization of dietary lipids in preterm born infants which comprises administering to a preterm born infant in need of such improvement an effective amount of bile-salt stimulated lipase as described above.

Throughout this description the terms "standard protocols" and "standard procedures", when used in the context of molecular cloning techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

EXAMPLES

1. Preparation of Genetic Material

The plasmid pS452 (deposited under the Budapest Treaty with accession number DSM 7499) was used. This construct has a genomic fragment of BSSL (SEQ ID NO: 1) inserted into the first exon of the murine WAP gene (Strömqvist et al., 1996). The features of pS452 is further shown in FIG. 1 and Table I.

The plasmid DNA was introduced into the E coli strain DH5α by standard transformation methods. Twelve clones were screened for the presence of pS452 and all contained the plasmid. DNA from clones 5–8 was pooled and renamed pBSSLI. This miniprep DNA was used for subsequent manipulations.

Figure 2:
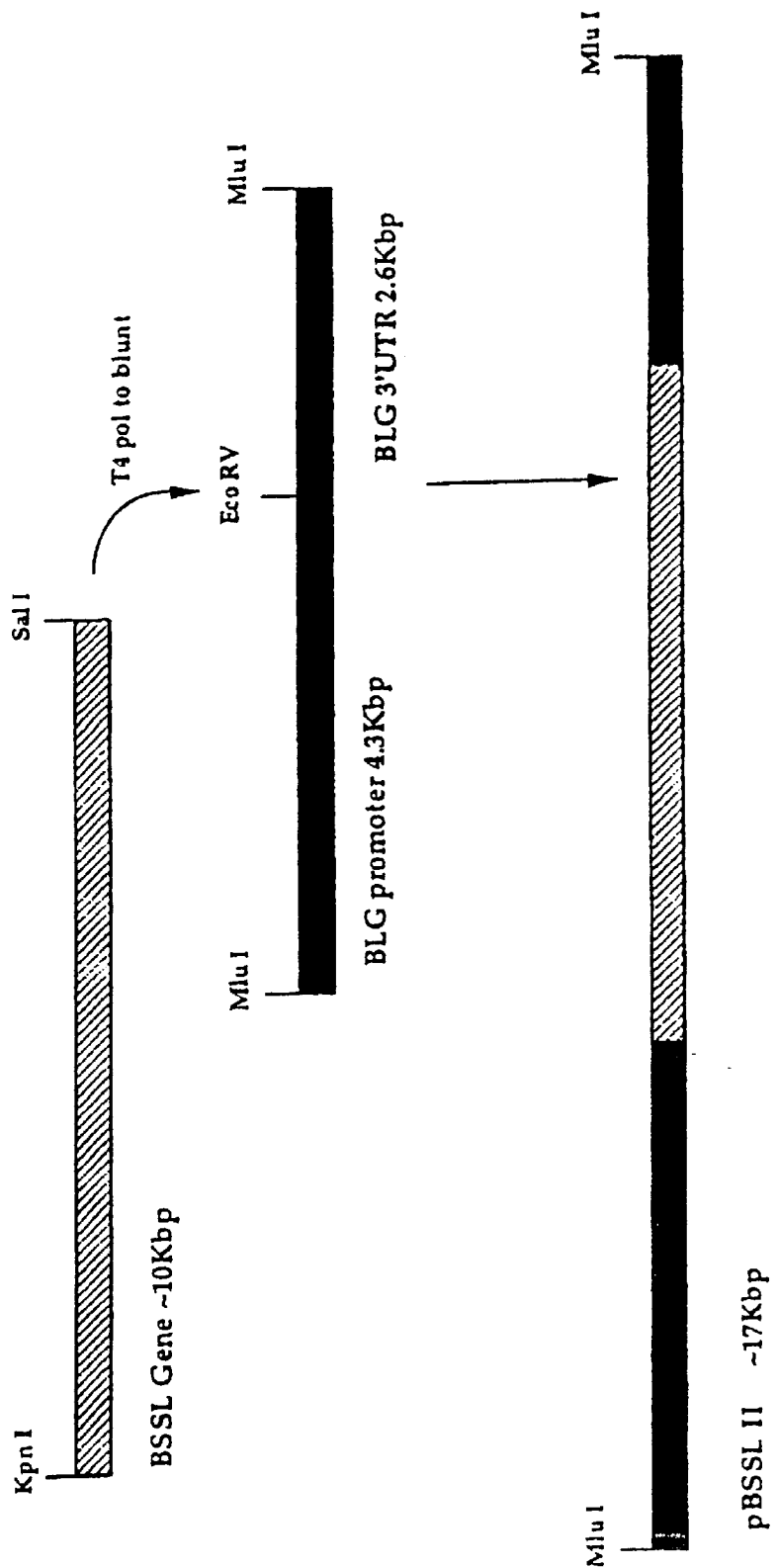
FIG. 2. Schematic view of the construction of the clone pBSSLII.

1.1 Subcloning of BSSL Sequences into pMAD6 pBSSLI was restricted with KpnI and SalI in order to excise the BSSL genomic sequences. The DNA was phenol extracted, ethanol precipitated and resuspended in water. The digest was treated with $T_4$ DNA polymerase to produce blunt ends. The DNA was size fractionated on a 0.5% agarose gel and the band corresponding to BSSL excised and purified using the Prepagene system (Biorad). Purified BSSL fragment was ligated into the EcoRV site of the BLG vector pMAD6 (see FIG. 2) and transformed into E. coli DH5a by standard techniques. Bacterial colonies were screened by a standard alkaline lysis miniprep method. Colonies were initially screened with HindiII to visualize BSSL insertion and orientation.

1.2 Preparation of Plasmid DNA

The correct orientation and integrity of clones corresponding to a BLG/BSSL hybrid were confirmed by restriction digest with the enzymes BamHI, HindIII, MluI, NcoI, SphI, StuI and XbaI. One clone was chosen and named pBSSLII. DNA from pBSSL II was prepared by standard alkaline lysis followed by CsCl gradient ultracentrifugation.

1.3 Confirmation of the Structure of pBSSLH

The new junction sequences were confirmed initially by double stranded DNA sequencing using primers reading across the EcoRV site in pMAD6. Subsequently, the entire exon coding parts of pBSSLII were completely sequenced in order to confirm its structure. Sequences were obtained using an ABI377 automatic sequencing machine and associated double strand sequencing technologies. The sequence data was compiled into its final form using the Autoassembler™ (ABI) program and aligned against the expected DNA sequence. There were no changes from the expected DNA sequence. In order to confirm that all of the repeat structure of BSSL was present in the plasmid, this region was sequenced from both sides. It was confirmed that all 16 of the 33 base pair repeats (corresponding to the 11 amino acid repeat) were present in the construct.

1.4 Preparation of DNA for Injection

The BSSL II transgene was excised from its bacterial vector backbone by restriction with MluI. DNA for microinjection was separated from vector backbone by rate zonal ultracentrifugation in 20–40% linear sucrose gradients. Fractions from the gradients were analyzed by agarose gel electrophoresis and vector free insert fractions pooled. DNA was ethanol precipitated and resuspended in water. Pooled BSSL II DNA was subjected to a second round of sucrose density gradient ultracentrifugation in order to minimize bacterial vector contamination. The concentration of the final product was determined by ultraviolet spectrophotometry using the GeneQuant II instrument (Pharmacia) and the DNA checked by agarose gel electrophoresis.

2. Production of Transgenic Sheep 2.1 Source and Organization of the Animals

The study used only adult ewes and adult rams of the Poll Dorset breed which had been resident at PPL Therapeutics, East Mains, Ormiston, since their importation from New Zealand or which were born at East Mains. All ewes were more than 12 months old at the start of the study. All rams had proven fertility during 1994.

Ewes and ewe hoggs of the Poll Dorset breed or Poll Dorset cross breed which had been resident at PPL Therapeutics, East Mains, Ormiston since their importation from New Zealand or which were born at East Mains or Poll Dorset ewes and ewe hoggs imported from New Zealand.

The study was divided up first by week (1 5) and then further subdivided into four injection groups. Each group had 7 donors and 25 recipients.

2.2 Methods 2.2.1 Donors

All ewes were treated with an intravaginal progesterone impregnated sponge (Chronogest Goat Sponge—Intervet) on the start date, day −13, −14, −15 or −16. These were left in situ for 12 to 15 days and removed on day −1.

Donors were treated with a total of 1.0 units of ovine follicle stimulating hormone (OFSH) (Ovagen, Immuno- Chemical Products Ltd), given over four days, starting on day −4 and finishing on day 0. Donors were also treated with 400 IU of a follicle stimulating hormone substitute (PMSG-Intervet) on day −3 to provide additional follicle stimulating and luteolysing activity.

Donors were injected intramuscularly with 2 ml of a synthetic releasing hormone analogue (Receptal-Hoescht Animal Health) on day 0.

Donors were fertilized by intrauterine artificial insemination (AI). All rams used for AI were semen assessed prior to the start of the study. Donors were starved of food and water for at least 12 hours before AI and artificially inseminated by intrauterine laparoscopy under general anaesthesia (GA) on day 1.

GA was induced by an intravenous injection of 5% thiopentone sodium (Intraval Sodium, RMB Animal Health Ltd) and maintained by inhalation of 1–2% Halothane/$O_2$/$N_2O$ after intubation. AI was carried out using freshly collected semen from a Poll Dorset ram. Semen was diluted with equal parts of sterile phosphate buffered saline or Ultra Heat Treated Milk (Anchor Standard Milk from New Zealand) and 0.2 ml of the diluted semen injected per uterine horn.

Embryos were recovered from donors on day 2. Donors were starved of food and water from day 1. Embryo recovery was carried out by GA (as in 2.2.1.5). Donors were allowed to recover after an intramuscular injection of Temgesic (Reckitt and Colman) and an intramuscular injection of Amoxypen LA (Mycofarm UK Ltd) at the manufacturers recommended dose rate before transfer to the surgery.

A laparotomy incision was made and the uterus exteriorized. Embryos were recovered by retrograde flushing of the oviducts with Ovum Culture Medium (Immuno-Chemical Products Ltd). After flushing, the uterus was returned to the abdomen and the incision closed.

2.2.2 Embryo Microinjection

All one cell embryos with visible pronuclei were microinjected into one pronucleus with approximately 2 pl of DNA from a solution at 6 µg/ml in TE (10 mM Tris, pH 7.5/0.1 mM EDTA). The DNA was prepared and diluted to approximately 6 µg/ml, stored frozen at −20° C. in 40 µl aliquots. A photographic record of the quality of the DNA preparation used was made, prior to aliquoting and subsequent microinjection.

On each microinjection day an aliquot of the DNA was removed from the freezer and allowed to thaw at room temperature. The aliquot was labelled with the group number and used for microinjection on that day only. Any DNA remaining after microinjection was refrozen at −20° C. and stored for subsequent analysis. At the end of each week these frozen aliquots of "used" DNA were analyzed by electrophoresis and photographed.

2.2.3 Recipients (a) Sponging

All recipients had an intravaginal progesterone impregnated sponge (Chronogest Ewe Sponge—Intervet) inserted on the start date, day −13, −14, −15 or −16. These were left in situ for 12–15 days and removed on day −1.

Recipients received 2.0 ml (400 IU) of a follicle stimulating hormone substitute (PMSG—Intervet) intramuscularly at sponge removal on day −1. If the sponge was missing the ewe received 0.5 ml Estrumate and not PMSG.

Recipients were tested for oestrus with a raddled vasectomized ram between 0800 and 1700 hours on days 0 and 1. The vasectomized ram may run permanently or intermittently with the ewes throughout this period. Ewes were checked at least twice daily for onset of oestrus.

(b) Recipient Transfer

Embryos surviving microinjection were returned to recipients on day 2. Recipients were starved from day 1. Embryo return was carried out under general anaesthesia and analgesia (as in 2.2.1.5). The uterus was exteriorized via a laparotomy incision. Embryos were returned to one or both oviducts only in ewes with at least one suitable corpora lutea. After replacement of the uterus the abdomen was closed and the recipients allowed to recover.

All transferred recipients were ultrasonically scanned for pregnancy and number of foetuses carried between the 50th and 90th days of pregnancy, Day 50–90.

The pregnant recipients were vaccinated against erysipelas, using Erysorb ST (Hoechst Animal Health) and against clostridial disease and pasteurellosis using Heptavac P (Hoechst Animal Health). They either received a single booster dose of each vaccine or a primary course of two injections depending on their previous vaccination history. All vaccinations were carried out according to manufacturer's instructions.

(c) Lambing

If the ewe had not already lambed, lambing was induced at 1400 hours on Day 145 of pregnancy by an intramuscular injection of 8 ml Soludex (Mycofarm).

Twenty-four hour supervision of lambing was provided. Recipient ewes were placed in an individual pen with their lambs as soon as possible after lambing, and remained individually penned for at least 24 hours post-lambing. The afterbirths were removed from the individual pens as soon as possible after their expulsion by the ewe.

All lambs were identified by an ear tag bearing their individual number in each ear and by a transponder in the left groin. Lambs were ear tagged before they left the individual pens.

All lambs were left with their dams for rearing. Ewes and lambs may remain housed and fed complete diet, concentrates, other supplements and/or ad lib straw or may go out to grass. If necessary, the lambs were treated with an appropriate insecticidal pour-on product before being turned out to grass.

(d) Lambs—Tail Sampling

All lambs had a sample of tail tissue taken within the first week of life, unless this would prejudice their health, in which case sampling, was delayed until the lamb was considered well enough.

A burdizzo (The Ritchey Nipper, Ritchey Tagg Ltd) was applied to the tail below, but as close as possible to, the ring. The jaws of the burdizzo were closed and held firmly shut. The jaws were then opened and the burdizzo removed. Using a pair of scissors or scalpel blade the tail was removed at the level of the crush mark left by the burdizzo. As soon as the tail was removed the tip was shaved up and a 1 cm length cut off the tip. The 1 cm length tip was placed into a plastic bijou. Tail samples were analyzed as soon as possible after their collection for the presence of the transgene.

Immediately after the removal of the tail the lamb was given an intramuscular injection of Duphapen LA (Solvay Duphar) at the manufacturers recommended dose rate and the cut end of the tail was treated with an antibiotic spray or powder.

All lambs born dead or dying before tail sampling had samples of tail taken and frozen as soon as possible after death. Tail samples were also taken from lambs in utero of dead recipient ewes. The samples were frozen at −20° C. or below as soon as possible after they have been taken.

(e) Lambs—Blood Sampling

All lambs had a blood sample taken from the jugular vein into an EDTA vacutainer at 14 days of age or older, unless this would prejudice their health, in which case sampling was delayed until the lamb was considered fit enough.

2.3 Induction of Lactation and Milking of G0 Females

On days 1–7 Oestradiol Benzoate (5 mg/ml—Intervet) and Progesterone (25 mg/ml—Intervet) were injected subcutaneously. On days 18–20, Dexamethasone (Soludex Injection -Mycofarm) was injected intramuscularly once daily.

The udder of each ewe lamb was examined for mammary development and milk secretion on Day 21. Lactation should begin on Day 21. If milk was produced, all of it was collected from each half of the udder by expressing the milk into 50 ml Falcon tubes. Milk from the 2 halves may be bulked together. The total volume collected at each milking was recorded. Milking was then continue twice daily.

Milk (0.5 –1.0 ml) from each milking was taken from the bulk milk sample and placed in a plastic bijou. All milk was placed in a −20° C. freezeer until required for analysis.

3. Analysis of Sheep Samples for the Presence of the Transgene

Two tissues are routinely sampled and analyzed for the presence of the transgene, blood and tail. In general, the tail material is made available prior to blood and thus tail is analyzed first. The gap between delivery of the two samples is around one week and therefore tail and blood samples are never assayed in the same experiment. This provides some degree of safety and reduces the likelihood of discarding a positive animal as negative.

3.1 Processing Lamb Tail Samples

Roughly 10 mm$^3$ of sheep tail was placed into 1 ml Tail Buffer (0.3 M sodium acetate /50 mM KC/1.5 mM MgCl$_2$/ 10 mM Tris (pH 8.5) 0.5% NP40 /0.5% Tween-20) in a plastic bijou. Proteinase K (Boehringer Mannheim) was added to a final concentration of 0.5 mg/ml and the samples incubated at +55° C., with vigorous shaking, overnight.

Approximately 1 ml of digested tail material was extracted first with phenol and then CHCl$_3$/Isoamyl alcohol (24:1) before isopropanol precipitation, ethanol wash and air drying. Precipitated DNA was resuspended in 50–200 μl of water.

3.2 Processing Lamb Blood Samples

The Nucleon™ Kit (Scotlab) was used to purify DNA from the white cells in whole blood, according to the manufacturer's instructions. Basically, the method uses sodium perchlorate to solubilize protein and a silica matrix to capture the DNA. Approximately 1.5 ml of whole blood was extracted. The DNA was resuspended in 50 μl of TE (10 mM Tris, pH 8.0/1 mM EDTA).

3.3 Analysis of DNA by Southern Blotting

15 μl of each sample was cut with the restriction enzyme BamHI, according to the manufacturers instructions. Restricted DNA samples were quantified using the GeneQuant II instrument (Pharmacia) and aliquots corresponding to 10 μg of material were electrophoresed on a 1% agarose gel. Fractionated DNA was transferred to a nylon membrane support (Duralon-UV, Stratagene) by capillary transfer and crosslinked to the support by UV light.

Approximately 20 ng of a 1.8 kbp BamHI/EcoRV fragment, encoding the first 1.8 kbp of the BLG promoter, was radiolabelled with [α-$^{32}$P]dCTP using a random prime labelling kit (Boehringer Mannheim). Probe and membranes were hybridized in roller bottles, in a buffer 7% SDS/0.5 M NaP$_i$/1 mM EDTA (pH 7.2), for 12–16 hours at +65° C. Excess probe was removed by stringent washes and signal determined by autoradiography.

4. Analysis of Milk Samples for the Presence of Recombinant BSSL

1 μl and 0.1 μl of each sheep milk sample was introduced into 10 μl of 2×reducing sample buffer and loaded on to Novex 4–12% linear gradient gels (SDS-PAGE). Control sheep milk and native BSSL were loaded in the same manner. Native BSSL, prepared according to Hansson et al. (1993) and Bläckberg et al. (1995) acted as a standard and was loaded at a concentration of 0.2 mg/ml. Gels were run at 150 V and stained with Coomassie Brilliant Blue. Proteins were visualized after destaining. Approximate quantitation was achieved by comparison with known masses of native BSSL.

5. Results from the Sheep Study 5.1 Embryology

A summary of the lambing results is presented in Table II.

5.2 Screening

Figure 3:
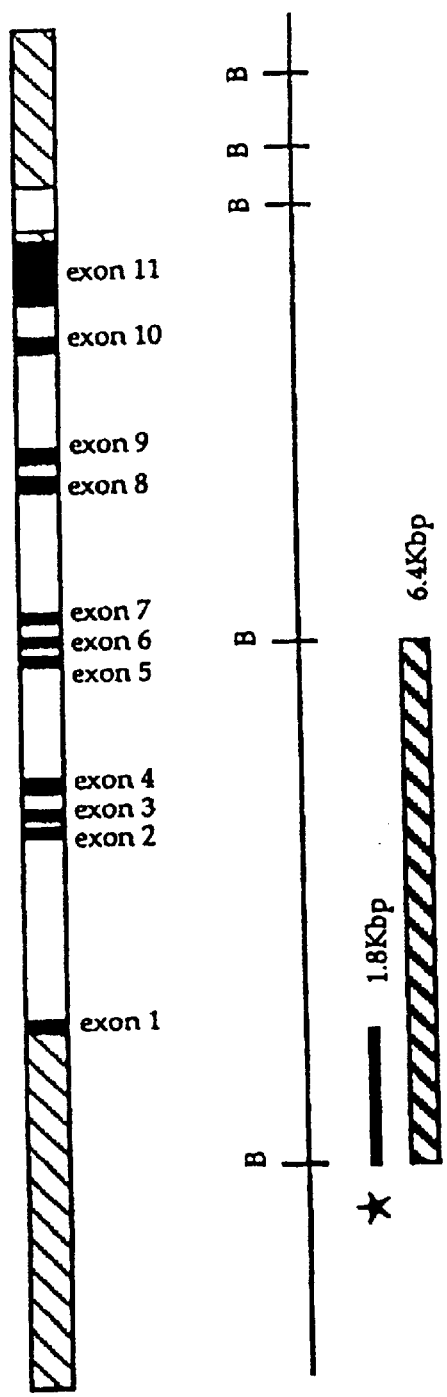
FIG. 3. Schematic view of the structure of pBSSLII.

A diagrammatic representation of the construct is shown in FIG. 3. The bar, labelled ⌈, represents the labelled probe, which is specific for the BLG promoter. This probe will anneal to the endogenous BLG gene and the transgene, if present. The size of the hybridizing transgene band is 6.4 kbp. B =BamH I.

Animals determined to be transgenic from tail DNA, blood DNA or both were subjected to a second round of analysis with a single Southern blot containing both tissue samples. It was shown that the four females have a relatively low transgene copy number. Some of the males, in particular 60232 and 60364 had copy numbers which may be considerably greater than 10. All animals were positive in both tail and blood samples.

A summary of the transgenic data is shown in Table II, thirteen animals in total, four females and nine males. The levels of transgenesis seen in this study, as a function of live births, are comparable to the highest levels of transgenesis that have been obtained in sheep. There is no data to suggest that the skew towards male animals is anything other than chance.

6. Milk Analysis 6.1 Induced Lactation

Four ewe lambs, transgenic for hBSSL, were induced to lactate, their numbers and ages are outlined in Table III. In addition, a non-transgenic ewe lamb of similar age was induced as a negative control. All five lambs produced milk. The daily volumes were recorded. All lambs gave several hundred ml of induced milk (total volume between 190 to 2100 ml during 26 days of lactation).

6.2 Levels of Human BSSL in Milk

Analysis of the expression of hBSSL in sheep milk shows that a 107 IcDa protein, corresponding to the BSSL standard, was present in all four transgenic milks, but not the negative control. The levels of the protein in the milk of 60276 did not vary greatly across the period of the lactation.

7. Biochemical Characterization 7.1 Proteins Used

Native BSSL from human milk as well as recombinant BSSL produced in CHO, C127 and E. coli were isolated and purified as described by Hansson et al. (1993) and Bläckberg et al. (1995).

7.2 Purification of BSSL from Sheep Milk

Sheep milk samples were collected from the four sheep (cf. Section 6.1) that were found to carry the human BSSL gene, as well as from the non-transgenic sheep. The milk was centrifuged at approximately 10,000×g for 2 h and the supernatant was poured through a sheet of Kleenex wipe to remove fat flakes/droplets on the surface. The volume of the supernatant was measured and CaCl$_2$ to a final concentration of 60 mM was added, the pH was adjusted to 4.3 by the addition of HCl and the samples were stirred overnight in the cold. $Na_2HPO_4$ was added to a concentration of 50 mM and the pH was raised to 7.4. The samples were centrifuged at 15,000×g for 45 min and the supernatants were collected.

The supernatants (whey) from one of the ewes were pooled for purification and diluted with 2 volumes of 5 mM barbiturate, 50 mM NaCl and applied to Heparin-Sepharose® and BSSL was purified as described by Bläckberg and Hernell (1981). For further purification, the pooled protein from the Heparin-Sepharose® was applied to a Superdex 200 size-exclusion chromatography column.

The profile obtained on Heparin-Sepharose resembled that obtained with native BSSL as well as that with recombinant full-length BSSL produced in mammalian cells. The BSSL-containing fractions were pooled and collected for a second chromatography on a Superdex 200 column. Upon this chromatography, two major peaks containing BSSL-activity were identified. When these peaks were analysed by SDS-PAGE, the peak eluting at approx. 40 min migrated as a protein of approximately the same apparent molecular mass as recombinant BSSL produced in mammalian cell culture did, while the other component eluting at approximately 50 min migrated as a considerably smaller protein (~80 kDa), probably corresponding to endogenous sheep BSSL. Both bands were fuzzy compared to the bands of the standard indicating the presence of glycosylation.

7.3 SDS-PAGE and Western Blotting

SDS-PAGE was performed by using precast gels in a Laemmli system. Western blotting was performed using antibodies against the complete protein, against amino acids 40–56, 1–535 and 712–722 as well as antibodies against the repeat part of the protein.

Milk samples were analysed by western blotting using antibodies directed against native (full-length) BSSL. All positive milk samples showed a strong band at the molecular mass where C127-produced BSSL could be seen, while the control milk lacks this band. It was concluded that the transgenic sheep express human BSSL protein in their milk at readily detectable levels.

7.4 Analysis of BSSL Activity in Sheep Milk

Figure 4:
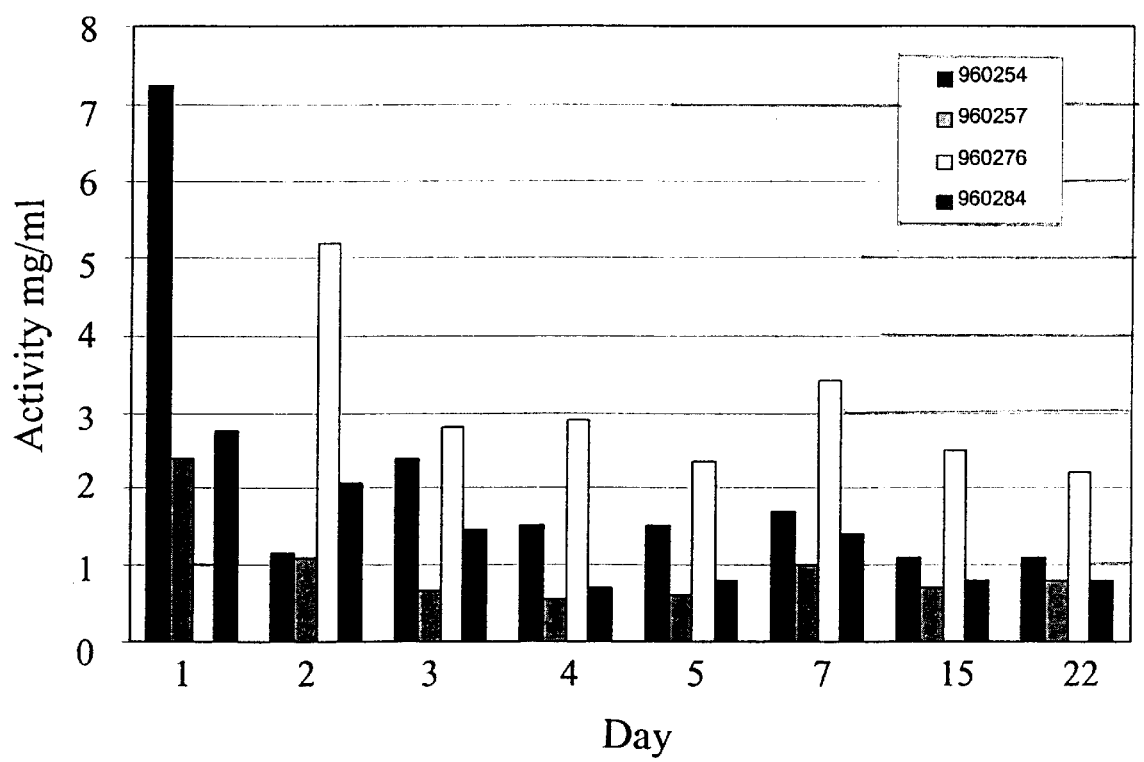
FIG. 4. BSSL activity in transgenic sheep.

The whey was diluted 50 times with $H_2O$ and the activity was measured as described by Bläckberg et al. (1995). From the first week of lactation, all milks were analysed each day while for the rest of the lactation period only one milk sample per week was analysed. (FIG. 4) The sample of 9 September from the sheep designated 60254 is most certainly overestimated since the volume was difficult to determine in this sample. The highest values overall were obtained with samples collected from sheep 60276.

7.5 Functional Properties of BSSL

The protease resistance, the pH-stability, the temperature resistance and the bile salt-stimulation was performed as described by Bläckberg et al. (1995). Upon analysis of recombinant BSSL, no differences in the pH-dependence, temperature stability, the bile salt-stimulation and the protease resistance could be seen.

7.6 Monosaccharide Composition

After running the samples on a SDS-gel and transferring the separated proteins to a PVDF membrane, the membrane was washed in $H_2O$ and incubated with neuraminidase in order to remove terminal sialic acids. (Sigma N-2133) at a concentration of approximately 500 U /ml in 0.1 M Tris, pH 6.5. For confirmation of O-glycosylation, the reaction with digoxygenin-labelled peanut lectin (PNA) was analysed (see Strömqvist et al., 1996).

The monosaccharide composition was studied by gas chromatography and by sialic acid determination according to methods known in the art (Landberg et al., 1997).

Table IV shows the monosaccharide composition of BSSL produced in transgenic sheep compared to BSSL produced in cell culture (CHO and C127 cells) and to three different samples of human native milk BSSL isolated from donated milk from three different mothers in different stages of lactation (Landberg et al., 1997). All samples of native BSSL contain fucose and the total content of monosaccharide varies from 19% to 34%. In contrast, the cell culture and sheep isolated recombinant BSSL contain no fucose but a higher content of sialic acid. It can be concluded that human BSSL from transgenic sheep appears to be very similar to the cell culture produced protein, both in total content of monosaccharides (23%) and in monosaccharide composition.

Deposit of Biological Material

The plasmid pS452 has been deposited in accordance with the Budapest Treaty at the Deutsche Sammlung von Mikroorganismen und Zellkulturen (DSMZ) on Feb. 26, 1993 with accession number DSM 7499.

REFERENCES

Ali, S. & Clark, A. J. (1988) J. Mol. Biol. 199, 415–426.
Archibald, A. L. et al. (1990) Proc. Natl. Acad. Sci. USA 87, 5178–5182.
Baba, T. et al. (1991) Biochemistry 30, 500–510.
Bläckberg, L. and Hernell, O. (1981) Eur. J. Biochem. 116, 221–225.
Bläckberg, L. et al. (1995) Eur. J. Biochem. 228, 817–821.
Bosner, M. S. et al. (1988) Proc. Natl. Acad. Sci. U.S.A. 85(20), 7438–7442.
Bradley, A. (1991) Curr. Opinion Biotechnol. 2, 823–829.
Brinster, R. L. et al. (1988) Proc. Natl. Acad. Sci. U.S.A. 85, 836–840.
Carver, A. et al. (1992) Cytotechnology 9, 77–84.
Carver, A. et al. (1993) Biof/Technology 11, 1263–1270.
Chada, K. et al. (1985) Nature 314, 377–380.
Clark, A. J. et al. (1989) Bio/Technology 7,487–492.
Cooper, J. D. & Dalrymple, M. A. (1994) The Japanese Journal of Experimental Medicine, Developmental Biotechnology Supplement, 12, No.2, 124–132:
Ebert, K. M. et al. (1991) Bio/Technology 9, 835–838.
Evans. M. J. & Kaufman, M. H. (1981) Nature 292, 154–156.
Fujiwara, Y. et al. (1997) Molec. Reprod. & Devel. 47, 157–163.
Gilboa, E. et al. (1986) Biotechniques 4, 504–512.
Hansson, L. et al. (1993) J. Biol. Chem. 268, 26692–26698.
Harris, S. et al. (1991) Developmental Genetics 12, 299–307.
Hennighausen, L. et al. (1990) Current Opinion in Biotechnology 1, 74–78.
Hogan, Constantini & Lacy: "Manipulating the Mouse Embryo" ($2^{nd}$ ed.) CSHP, Cold Spring Harbor, N.Y., USA, 1994.
Hooper, M. L.: "Embryonal Stem Cells: Introducing planned changes into the animal germline", Harwood Academic, Chur, Switzerland, 1992.
Jaensich, R. et al. (1975) Proc. Natl. Acad. Sci. U.S.A. 72, 4008–4012.
Landberg, E. et al. (1997) Archives of Biochemistry and Biophysics 344, 94–102.
Lavitrano, M. et al. (1989) Cell 57, 717–723.
Lidberg, U. et al. (1992) Genomics 13, 630–640.
Loomes, K. M. & Senior, H. E. J. (1997) FEBS Letters 405, 369–372.
Manson, A. L. et al. (1997) EMBO J. 16, 4238–4249.
McWhir, J. et al. (1996) Nature Genetics 14, 223–226.

Nilsson, J. et al. (1990) Eur. J. Biochem. 192, 443–550.

Reue, K. et al. (1991) J. Lipid Res. 32, 267–276.

Robertson, E. J. "Embryo-derived Stem Cells" in: "Teratocarcinomas and Embryonic Stem Cells, A Practical Approach", Robertson, E. J. (Ed.), pp 71–112, IRL Press, Oxford, 1987.

Schedl, A. et al. (1993) Nature 362, 258–261.

Schnieke, A. E. et al. (1997) Science 278, 2130–2133.

Simons, J. P. et al. (1987) Nature 328, 530–532.

Simons, J. P. et al. (1988) Bio/Technology 6, 179–183.

Spilburg, C. A. et al. (1995) Biochemistry 34, 15532–15538.

Stacey, A. et al. (1994) Mol. Cell. Biol. 14, 1009–1016.

Stacey, A. et al. (1995) Proc. Natl. Acad Sci. U.S.A. 92, 2835–2839.

Strömqvist, M. et al. (1995) J. Chromatography 718(1), 53–58.

Strömqvist, M. et al. (1996) Transgenic Research 5, 475–485.

Umland, T. et al. "Transgenic Animals—Generation and Use", Harwood Academic Publishers, Chur, Switzerland, 1996

Velander, W. H. et al. (1992) Proc. Natl. Acad. Sci. USA 89, 12003–12007.

Wang, C-S. & Johnson, K. (1983) Anal. Biochem. 133, 457–61.

Wang, C-S & Hartsuck, J. A. (1993) Biochim. Biophys. Acta 1166, 1–19.

Wang, C-S. et al. (1995) Biochemistry 34, 10639–10644.

Whitelaw et al. (1991) Transgenic Research 1, 3–13.

Wilmut, I. et al. (1997) Nature 385, 810–813.

Wright, G. et al. (1991) Bio/Technology 9, 830–834.

TABLE I

Features of plasmid pS452

| Consituents | Size of fragments | Sites | Genetic markers |
|---|---|---|---|
| pUC 19 | 2.7 | NotI | ampR |
| murine WAP, 5'-flank and 5'-untranslated region | 4.1 | NotI/KpnI | |
| human BSSL structural gene | 9.9 | KpnI/SalI | |
| murine WAP, structural gene and 3'-flank | 4.3 | SalI/NotI | |

TABLE II

Summary of Sheep Study

| | No. Live Lambs | | | No. Transgenic Lambs | | | % Transgenics/ |
|---|---|---|---|---|---|---|---|
| Week | male | female | Total | male | female | Total | livebirths |
| 1 | 16 | 18 | 34 | 2 | 0 | 2 | 5.9 |
| 2 | 23 | 31 | 54 | 2 | 0 | 2 | 3.7 |
| 3 | 17 | 23 | 40 | 3 | 2 | 5 | 12.5 |
| 4 | 13 | 21 | 34 | 1 | 2 | 3 | 8.8 |
| 5 | 12 | 17 | 29 | 1 | 0 | 1 | 3.4 |
| Totals | 81 | 110 | 191 | 9 | 4 | 13 | 6.8 |

TABLE III

Ewe-lamb Data

| Lamb | Birth Date | Age on Induction | Age on First Milk |
|---|---|---|---|
| 60276 | Apr. 11, 1996 | 131 days | 151 days |
| 60284 | Apr. 13, 1996 | 129 days | 149 days |
| 60254 | Apr. 2, 1996 | 140 days | 160 days |
| 60257 | Apr. 5, 1996 | 137 days | 157 days |

TABLE IV

Monosaccharide composition
The values are expressed as mass per cent of the total mass of BSSL, based on the amino acid sequence.

| | Fuc | Gal | Man | GalNac | GlcNac | Neu5Ac | Total |
|---|---|---|---|---|---|---|---|
| 1 | — | 7.5 | 1.5 | 6.3 | 4.2 | 3.1 | 23 |
| 2 | — | 5.4 | 0.55 | 3.5 | 1.8 | 8.9 | 20 |
| 3 | — | 4.2 | 0.64 | 4.2 | 0.84 | 4.3 | 14 |
| 4 | 5.5 | 11 | 0.36 | 1.7 | 7.8 | 1.8 | 29 |
| 5 | 3.5 | 6.5 | 0.22 | 1.2 | 5.2 | 2.0 | 19 |
| 6 | 3.7 | 12 | 0.48 | 1.7 | 12 | 3.2 | 34 |
| 7 | | | | | | | not detectable |

Row
1: Human BSSL from transgenic sheep
2: Human BSSL produced in cultured C127 cells
3: Human BSSL produced in cultures CHO cells
4: Human native BSSL (individual 1)
5: Human native BSSL (individual 2)
6: Human native BSSL (individual 3)
7: Human BSSL produced in transgenic mice (cf. Strömqvist et al., 1996)

Abbreviations

Fuc, fucose; Gal, galactose; Man, mannose; GalNac, N-acetylgalactosamine; GlcNac, N-acetylglucosamine; Neu5Ac, 5-Ac-neuraminic acid.

What is claimed is:

1. A transgenic sheep, wherein a transgene, comprising a nucleotide sequence encoding a recombinant human bile salt-stimulated lipase operatively linked to a milk-protein promoter, has been integrated into the genome of the germ and somatic cells of the transgenic sheep, wherein the recombinant human bile salt-stimulated lipase consists of an amino acid sequence set forth as SEQ ID NO: 3 or SEQ ID NO: 4, wherein the human bile salt-stimulated lipase is capable of being expressed in the mammary gland of the transgenic sheep, and wherein the human bile salt-stimulated lipase expressed in the mammary gland is O-glycosylated.

2. A transgenic sheep according to claim 1, wherein the nucleotide sequence encoding the recombinant human bile salt-stimulated lipase is carried by the plasmid pS452, identified by accession number DSM 7499.

3. A transgenic sheep according to claim 1, wherein the nucleotide sequence encoding the recombinant human bile salt-stimulated lipase is the nucleotide sequence set forth as SEQ ID NO: 1 or SEQ ID NO: 2.

4. A transgenic sheep according to claim 1, wherein the promoter is a β-lactoglobulin promoter.

5. A transgenic sheep according to claim 1, wherein the transgenic sheep is a female transgenic sheep, wherein the nucleotide sequence encoding the human bile salt-stimulated lipase is expressed in the mammary gland of the female transgenic sheep, and wherein the human bile salt-stimulated lipase is present in the milk of the female transgenic sheep.

6. A process for production of a transgenic sheep according to claim 5, comprising:
(a) providing a nucleotide sequence encoding the human bile salt-stimulated lipase with an amino acid sequence set forth as SEQ ID NO: 3 or SEQ ID NO: 4, operatively linked to a milk-protein promoter functional in a sheep;
(b) introducing said nucleotide sequence into an embryo or fertilized egg of a sheep, so as to incorporate said nucleotide sequence into the germline nucleic acid of the embryo or fertilized egg;
(c) transplanting said embryo or fertilized egg into a pseudopregnant host sheep;
(d) allowing said host sheep to produce progeny; and
(e) selecting a female progeny sheep that produces human bile salt-stimulated lipase in its milk.

7. A process for production of human bile salt-stimulated lipase comprising
(a) producing milk in a female transgenic sheep as declined in claim 5;
(b) collecting the milk produced in step (a); and, optionally,
(c) isolating the human bile salt-stimulated lipase.

8. A process for production of human bile salt-stimulated lipase comprising:
(a) providing a nucleotide sequence encoding the human bile salt-stimulated lipase with an amino acid sequence set forth as SEQ ID NO: 3 or SEQ ID NO: 4, operatively linked to a milk-protein promoter functional in sheep;
(b) introducing said nucleotide sequence into an embryo or fertilized egg of a sheep, so as to incorporate said nucleotide sequence into the germline nucleic acid of the embryo or fertilized egg;
(c) transplanting said embryo or fertilized egg into a pseudopregnant host sheep;
(d) allowing said host sheep to produce progeny;
(e) selecting a female progeny sheep that produces human bile salt-stimulated lipase in its milk wherein the human bile salt-stimulated lipase is O-glycosylated;
(f) collecting the milk produced by the female sheep selected in step (e); and, optionally,
(g) isolating the human bile salt-stimulated lipase.

9. A process according to claim 6 or 8, wherein the nucleotide sequence encoding human bile salt-stimulated lipase is selected from the group consisting of:
(a) a nucleotide sequence carried by the plasmid pS452, identified by accession number DSM 7499;
(b) a nucleotide sequence set forth as SEQ ID NO: 1 or SEQ ID NO: 2; and
(c) a nucleotide sequence encoding a polypeptide set forth as SEQ ID NO: 3 or SEQ ID NO: 4.

10. A process according to claim 6 or 8, wherein the milk-protein promoter is a β-lactoglobulin promoter.

11. A process according to claim 9, wherein the milk-protein promoter is a β-lactoglobulin promoter.

* * * * *

UNITED STATES PATENT AND TRADEMARK OFFICE
CERTIFICATE OF CORRECTION

PATENT NO.    : 6,525,241 B1
DATED         : February 25, 2003
INVENTOR(S)   : Dalrymple et al.

It is certified that error appears in the above-identified patent and that said Letters Patent is hereby corrected as shown below:

<u>Title page,</u>
Item [30], Foreign Application Priority Data, replace "(CH)" with -- (SE) --.

Signed and Sealed this

Twenty-second Day of July, 2003

JAMES E. ROGAN
*Director of the United States Patent and Trademark Office*